United States Patent
LaVoie et al.

(10) Patent No.: US 6,740,650 B2
(45) Date of Patent: May 25, 2004

(54) HETEROCYCLIC CYTOTOXIC AGENTS

(75) Inventors: Edmond J. LaVoie, Princeton Junction, NJ (US); Leroy Fong Liu, Bridgewater, NJ (US); Younong Yu, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/134,983

(22) Filed: Apr. 29, 2002

(65) Prior Publication Data

US 2003/0100560 A1 May 29, 2003

(51) Int. Cl.[7] .................. A61K 31/5025; C07D 237/26; C07D 487/04; C07D 487/14; C07D 491/056
(52) U.S. Cl. .................. 514/228.2; 514/228.5; 514/233.2; 514/248; 544/60; 544/115; 544/233
(58) Field of Search .................. 544/233, 60, 115; 514/248, 228.2, 228.5, 233.2

(56) References Cited

U.S. PATENT DOCUMENTS

| | | | | |
|---|---|---|---|---|
| 2,915,523 A | 12/1959 | Moore et al. | | 260/279 |
| 2,981,731 A | 4/1961 | Moore et al. | | 260/239.1 |
| 2,985,661 A | 5/1961 | Hien et al. | | 260/309 |
| RE26,065 E | 7/1966 | Marvel et al. | | 260/47 |
| 3,267,107 A | 8/1966 | Sallay | | 260/287 |
| 3,272,707 A | 9/1966 | Tedeschi | | 167/65 |
| 3,449,330 A | 6/1969 | Guglielmetti et al. | | 260/240 |
| 3,538,097 A | 11/1970 | Lowe et al. | | 260/268 |
| 3,542,782 A | 11/1970 | Houlihan et al. | | 260/251 |
| 3,849,561 A | 11/1974 | Junzo et al. | | 424/258 |
| 3,884,911 A | 5/1975 | Shimada et al. | | 260/240 J |
| 3,912,740 A | 10/1975 | Zee-Chang et al. | | 260/286 |
| 4,559,157 A | 12/1985 | Smith et al. | | 252/90 |
| 4,608,392 A | 8/1986 | Jacquet et al. | | 514/844 |
| 4,761,477 A | 8/1988 | Ikekawa et al. | | 546/48 |
| 4,820,508 A | 4/1989 | Wortzman | | 424/59 |
| 4,925,943 A | 5/1990 | Kanmacher et al. | | 546/149 |
| 4,938,949 A | 7/1990 | Borch et al. | | 424/10 |
| 4,980,344 A | 12/1990 | Maroko | | 514/26 |
| 4,992,478 A | 2/1991 | Geria | | 514/782 |
| 5,106,863 A | 4/1992 | Hajos et al. | | 514/395 |
| 5,112,532 A | 5/1992 | Ninomiya et al. | | 252/587 |
| 5,126,351 A | 6/1992 | Luzzio et al. | | 514/291 |
| 5,190,753 A | 3/1993 | Behrens et al. | | 424/85.8 |
| 5,244,903 A | 9/1993 | Wall et al. | | 514/279 |
| 5,318,976 A | 6/1994 | Luzzi et al. | | 514/279 |
| 5,639,759 A | 6/1997 | Magolda et al. | | 514/285 |
| 5,646,283 A | 7/1997 | Suzuki et al. | | 546/61 |
| 5,767,142 A | 6/1998 | La Voie et al. | | 514/394 |
| 5,770,617 A | 6/1998 | LaVoie et al. | | 514/394 |
| 5,807,874 A | 9/1998 | LaVoie et al. | | 514/338 |
| 6,140,328 A | * 10/2000 | LaVoie et al. | | |

FOREIGN PATENT DOCUMENTS

| | | | | |
|---|---|---|---|---|
| EP | 0496634 | 7/1992 | | C07D/491/056 |
| GB | 2108955 | 5/1983 | | C07D/491/00 |
| RU | 1530628 | 12/1989 | | C07D/235/20 |
| WO | WO-92/21661 | 12/1992 | | C07D/221/18 |
| WO | WO-96/36612 | 11/1996 | | C07D/235/18 |
| WO | WO-97/29106 | 8/1997 | | C07D/455/02 |
| WO | WO-98/12181 | 3/1998 | | C07D/221/18 |
| WO | WO-98/31673 | 7/1998 | | C07D/235/18 |
| WO | WO-98/45272 | 10/1998 | | C07D/221/18 |

OTHER PUBLICATIONS

Altiparmakian et al., J.Chem. Soc. pp. 1112–1117 (1967).*
Dewar et al., J.Chem. Soc. p. 2201–2203 (1963).*
Gopinath et al. Indian J.Chem. p. 504–509 (1958).*
Aquirre, J. M. et al., "Reaction of 1,2–diarylethylamides with ethyl polyphosphate (EPP): correlation of the von Braun, Ritter and Bischler–Napieralski reactions", *Chemical Abstracts, 111* (13), Abstract No. 115004, (Sep. 25, 1989), pp. 25–27.
Arumugam, N., et al., "Synthesis of 7,8–Benzophenanthridines", *Indian Journal of Chemistry, 12*, (Jul. 1974),pp. 664–667.
Badia, D., et al., "Silicon–mediated isoquinoline synthesis: preparation and stereochemical characterization of 4–hydroxy–3–phenylisoquinolines", *Chemical Abstracts, 117* (13), Abstract No. 131034,(Sep. 28, 1992),p. 730.
Baezner, C., et al., "Uberfuhrung von o–nitro– und O,p–dinitro–benzylchlorid in acridinderivate", *Berichte der Deutschen Chemischn Gessellschaft, 39*, (1906),pp. 2438–2447.
Bathini, Yadagiri, et al., "Convenient Routes to Substituted Benzimidazoles and Imidazolo[4,5–b]pyridines Using Nitrobenzene as Oxidant", *Synthetic Communications, 20* (7), (1990),pp. 955–963.

(List continued on next page.)

*Primary Examiner*—Emily Bernhardt
(74) *Attorney, Agent, or Firm*—Schwegman, Lundberg, Woessner & Kluth, P.A.

(57) ABSTRACT

The invention provides compounds of formula I:

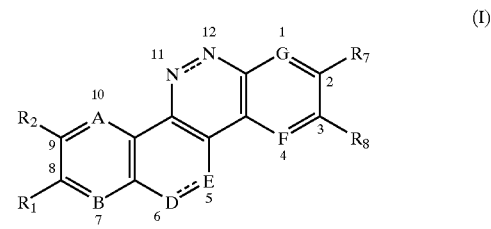

wherein
$R_1$–$R_8$ and A–G have any of the meanings defined in the specification and their pharmaceutically acceptable salts. The invention also provides pharmaceutical compositions comprising a compound of formula I, processes for preparing compounds of formula I, intermediates useful for preparing compounds of formula I, and therapeutic methods for treating cancer using compounds of formula I.

32 Claims, 11 Drawing Sheets

OTHER PUBLICATIONS

Bradsher, C. K., et al., ".alpha–Acyl–o–tolunitriles as intermediates in the preparation of 3–substituted isoquinolines and 1–amino–2–benzopyrylium derivatives", *Chemical Abstracts, 089 (21)*, Abstract No. 179810,(1978),pp. 3817–3820.

Buu–Hoi, N. P., et al., "Carcinogenic Nitrogen Compounds, XV. Polysubstituted Angular Benarcridines and Benzophenarsafzines", *Chemical Abstracts, 49*, Abstract, Col. 330c, (1955),1 p.

Buu–Hoi, Ng , "The chemistry of carcinogenic nitrogen compounds. Part V. Angular hydroxybenzacridines and hydroxydibenzacridines", *Journal of the Chemical Society, Letchworth GB*, (1950),pp. 2096–2099.

Buu–Hoi, Ng , et al., "The chemistry of carcinogenic nitrogen compounds. Part X. The Pfitzinger reaction in the synthesis of 1:2 benzacridines", *Journal of the Chemical Society, Letchworth, GB*, (1952),pp. 279–281.

Chen, Allan Y., et al., "A New Mammalian DNA Topoisomerase I Poison Hoechst 33342: Cytoxicity and Drug Resistance in Human Cell Cultures", *Cancer Research, 53 (6)*, Mar. 15, 1993),pp. 1332–1337.

Chen, Allan Y., et al., "DNA Minor Groove–Binding Ligands: A Different Class of Mammalian DNA Topoisomerase I Inhibitors", *Proc. Natl. Acad. Sci., USA, 90*, (Sep. 1993),pp. 8131–8135.

Chen, Allan Y., et al., "DNA Topoisomerases: Essential Enzymes and Lethal Targets", *Annu. Rev. Pharmacol. Toxicol., 34*, (1994),pp. 191–218.

Cherif, Abdallah, et al., "N–(5, 5–Diacetoxypent–1–yl)doxorubicin: A New Intensely Potent Doxorubicin Analogue", *J. Med. Chem., 35*, (1992), pp. 3208–3214.

Croisy, Martine , et al., "Synthesis and Carcinogenic Activity of Oxidized Benzacridines: Potential Metabolites of the strong carcinogen 7–Methylbenz[c]acridine and of the inactive isomer 12–methylbenz[a]acridine", *J. Med. Chem, 26*, (1983),pp. 303–306.

Croisy–Delcey, M. , et al., "Synthesis and Carcinogenic Activity of Oxidized Benzacridines: Potential Metabolites of the Strong Carcinogen 7–methylbenz[c]acridine and of the Inactive Isomer 12–methylbenz[a]acridine", *Chemical Abstracts, 98*, Abstract No. 43798,(1983),3 p.

D'Arpa, Peter , et al., "Topoisomerase–Targeting Antitumor Drugs", *Biochimica et Biophysica Acta, 989*, (1989),pp. 163–177.

Dominguez, E. , et al., "Dehydrogenation reactions of 1–substituted–3–aryltetrahydroisoquin oline derivatives", *Chemical Abstracts, 101 (11)*, Abstract No. 090742,(1984), pp. 525–528.

Dorofeenko, G. N., et al., "Synthesis of 3–aryl derivatives of 2–benzopyrylium salts with free.alpha–positions", *Chemical Abstracts, 074 (15)*, Abstract No. 076295,(1971),pp. 1013–1014.

Fitzgerald, J. J., et al., "Reaction of benzocyclobutene oxides with nitriles: synthesis of hypecumine and other 3–substituted isoquinolines", *Chemical Abstracts, 122(7)*, Abstract No. 081704,(Feb. 13, 1995),p. 1128.

Fox, G. J., et al., "para–Bromination of Aromatic Amines: 4–Bromo–N,N–Dimethyl–3–(Trifluoromethyl)Aniline", *Organic Synthesis, 55*, (1973),pp. 20–23.

Fujii, Noboru , et al., "Induction of Mammalian DNA Topoisomerase I–mediated DNA Cleavage and DNA Winding by Bulgarein", *Journal of Biological Chemistry, 268*, (1993),pp. 13160–13165.

Gallo, Robert C., et al., "Studies on the Antitumor Activity, Mechanism of Action, and Cell Cycle Effects of Camptothecin", *Journal of the National Cancer Institute, 46*, (Apr. 1971),pp. 789–795.

Gandhi, K. K., et al., "Regioselective thermal cyclization of 3–substituted arylenaminoimine hydrochlorides, a convenient method for the synthesis of functionalized polycyclic quinoline derivatives", *Heterocycles, 41 (5)*, (1995),pp. 911–920.

Garcia, A. , et al., "A simple direct approach to 1–substituted 3–arylisoquinolines from deoxybenzoins and nitriles", *Chemical Abstracts, 110 (25)*, Abstract No. 231407,(Jun. 19, 1989),pp. 6681–6686.

Gatto, Barbara , et al., "Identification of Topoisomerase I as the Cyctotoxic Target of the Protoberberine Alkaloid Coralyne", *Cancer Research, 56*, (1996),pp. 2795–2800.

Giovanella, Beppino C., et al., "Complete Growth Inhibition of Human Cancer Xenografts in Nude Mice by Treatment with 20–(S)—Camptothecin", *Cancer Research, 51*, (Jun. 1, 1991),pp. 3052–3055.

Hoan, Nguyen , et al., "Syntheses from o–halogenated anisoles and phenetoles", *Chemical Abstracts, 41 (20)*, Abstract No. 6571bg,(1947),1 p.

Iwao, Masatomo , et al., "A Regiospecific Synthesis of Carbazones via Consecutive Palladium–Catalyzed Cross–coupling and Aryne–Mediated Cyclization", *Heterocycles, 36*, (1993),pp. 1483–1488.

Izmail'Skii, V. A., et al., "Absorption Spectra of Molecular Complexes of Derivatives of Benzacridine and Dibenzacridine", *Chemical Abstracts, 54*, Abstract, Column 7335b, (1960),1 p.

Jacob, J. , et al., "Monooxygenase Induction by Various Xenobiotics and its Influence on Rat Liver Microsomal Metabolism of Chrysene in Comparison to Benz[a]anthracene", *Chemical Abstracts, 107*, Abstract No. 34760, (1987),2 p.

Janin, Yves L., et al., "Synthesis and Evaluation of New 6–Amino–Substituted Benzo[c]phenanthridine Derivatives", *J. Med. Chem, 36 (23)*, (1993),pp. 3686–3692.

Kametani, Tetsuji , et al., "Studies on the synthesis of heterocyclic compounds. DCXXVII. The formation of 2,3,9,10–tetramethoxybenz[c]acridine by treatment of 6,7–dimethoxy–1–(4,5–dimethoxy–2–nitrophen ethyl)–2methylisoquinoline with triethyl phosphite", *Chemical and Pharmaceutical Bulletin, 23 (9)*, (1975),pp. 2025–2028.

Kametani, T. , et al., "Synthesis of Heterocyclic Compounds, DCXXVII. Formation of 2,3,9,10–tetramethoxybenz[c]acridine by treatment of 6,7–dimethoxy–1–(4, 5–dimethoxy–2–nitrophenethyl)–2–methylisoquinoline with Triethyl Phosphite", *Chemical Abstracts, 84*, Abstract No. 43798,(1976),1 p.

Kanmacher, I. , et al., "Synthesis of Isoquino[1,2–b] quinazolines by Cycloaddition Reaction", *Chemical Abstracts, 114*, Abstract No. 207191,(1991).

Kar, G. K., et al., "Regioselective Thermal Cyclization of 3–substituted Arylenaminoimine Functionalized Polycyclic Quinoline Derivatives", *Chemical Abstracts, 123*, Abstract No. 111828,(1995), 1 p.

Kessar, S V., et al., "Azasteroids. Part VII. Synthesis of 7–hydroxy–2–methoxy–7,8,9,10–tetrahydrobenzo[i] phenanthridine", *J. Chem. Soc.*, (1971),pp. 259–261.

Kessar, S. V., et al., "New Routes to Condensed Polynuclear Compounds: Part X–Synthesis of Some Benzo[i]phenanthridines through Benzyne Cyclization", *Indian Journal of Chemistry*, 11, (Jul. 1973),pp. 624–627.

Kim, J. S., et al., "Influence of steric factors on topoisomerase I inhibition and cytotoxicity of bisbenzimidazoles related to Hoechst 33342", *Proceedings of the 86th Annual Meeting of the American Association for Cancer Research*, 36, Abstract No. 2689, Toronto, Ontario, Canada,(Mar. 1995),p. 451.

Kim, J. S., et al., "Steric factors associated with the topoisomerase I inhibition and cytotoxicity of substituted bisbenzimidazoles", *Abstract 10– Proceedings of the American Association of Pharmaceutical Scientists Eastern Regional Meeting*, (1995),p. 27.

Kim, Jung S., et al., "Structure–activity Relationships of Benzimidazoles and Related Heterocycles as Topoisomerase I Poisons", *Bioorganic & Med. Chem.*, 4, (1996),pp. 621–630.

Kim, Jung S., et al., "Substituted 2,5'–Bi–1H–benzimidazoles: Topoisomerase I Inhibition and Cytotoxicity", *J. Med. Chem.*, 39, (1996),pp. 992–998.

Kitamura, T. , et al., "Isoquinoline derivatives from the Ritter–type reaction of vinyl cations", *Chemical Abstracts*, 102 (1), Abstract No. 006157,(Jan. 7, 1985),pp. 1351–1354.

Klopman, G. , et al., "Testing by Artificial Intelligence: Computational Alternatives to the Determination of Mutagenicity", *Chemical Abstracts*, 118, Abstract No. 17489,(1993),1 p.

Lavoie, E. J., et al., "Structure–activity studies related to minor groove–binding ligands which inhibit mammalian DNA topoisomerase I", *Abstract 1—Proceedings of the 85th Annual Meeting of American Association for Cancer Research*, San Francisco, CA,(Apr. 1994),p. 2699.

Makhey, Darshan , et al., "Coralyne and Related Compounds as Mammalian Topoisomerase I and Topoisomerase II Poisons", *Bioorg. & Med. Chem. Lett.*, 4, (1996),pp. 781–791.

Makhey, Darshan , et al., "Protoberberine Alkaloids and Related Compounds as Dual Inhibitors of Mammalian Topoisomerase I and II", *Med Chem. Res.*, 5, (1994),pp. 1–12.

Meegalla, Sanath K., et al., "Synthesis and Pharmacological Evaluation of Isoindolo[1,2–b]quinazolinone and Isoindolo [2,1–a]benzimidazole Derivatives Related to the Antitumor Agent Batracylin", *J. Med. Chem.*, 37, (1994),pp. 3434–3439.

Memetzidis, G. , et al., "Structure–affinity relationships of berbines or 5,6,13,13a–tetrahydro–8H–dibenzo[a,g]quino lizines at.alpha.–adrenoceptors", *Eur. J. Med. Chem.*, 26, (1991),pp. 605–611.

Nelson, J. T., et al., "Proton and carbon–13 NMR spectra of fifteen substituted isoquinolines", *Chemical Abstracts*, 115 (5), Abstract No. 048721,(Aug. 5, 1991),1 p.

Peters, Dan , et al., "Synthesis of Various 5–Substituted Uracils", *J. Heterocyclic Chem.*, 27, (Nov./Dec. 1990),pp. 2165–2173.

Pilch, Daniel S., et al., "Biophysical Characterization of a Cytotoxic, Topoisomerase I Poison", *Abstract 8—Proceedings of the 3rd Annual Scientific Retreat of the Cancer Institute of New Jersey*, Princeton Marriott Forrestal Village, Princeton, NJ,(Jun. 1, 1995),p. 3.

Piper, J. R., et al., "Synthesis and Antifolate Activity of 5–Methyl–5,10–dideaza Analogues of Aminopterin and Folic Acid and an Alternative Synthesis of 5,10–Dideazatetrahydrofolic Acid, a Potent Inhibitor of Glycinamide Ribonucleotide Formyltransferase", *J. Med. Chem.*, 31, (1988),pp. 2164–2169.

Porai–Koshits, B. A., et al., "Imidazole derivatives Synthesis of some polybenzimidazoles", *J. Gen. Chem. USSR*, 23, As related in Chemical Abstracts, 48 (10) (1954), Col. 12740, (1953),pp. 873–879.

Quast, U., et al., "Heterocyclic.alpha.–carbinolamines with theisoquinuclidine skeleton. 3. Benzoisoquinuclidines", *Chemical Abstracts*, 097 (21), Abstract No. 182180,(1982), pp. 1501–1508.

Ramesh, D. , et al., "Studies on Polycyclic Azaarenes. 2. Sythesis of Trans–3,4–dihydroxy–3,–dihydrobenz[c]acridine and trans–8,9–dihydroxy–8,9–dihydrobenz[c]acridine", *Chemical Abstracts*, 118, Abstract No. 37626,(1988),2 p.

Ray, J. K., et al., "A Facile and Convenient Method for the Synthesis of 8–methoxy–10,11–dihydronaphtho[1,2–b] quinolines", *Chemical Abstracts*, 92, Abstract No. 76254, (1980),2 p.

Safaryan, G. P., et al., "2–Benzopyrylium salts. 25, Reaction of 2–benzopyrylium salts with some nucleophiles", *Chemical Abstracts*, 096 (17), Abstract No. 142656,(1982),pp. 1608–1611.

Schiess, P. , et al., "Thermolytic ring opening of acyloxybenzocyclobutenes: an efficient route to 3–substituted isoquinolines", *Chemical Abstracts*, 104 (19), Abstract No. 168332,(May 12, 1986),pp. 3959–3962.

Sethi, Manohar L., "Enzyme Inhibition VI: Inhibition of Reverse Transcriptase Activity by Protoberine Alkaloids and Structure–Activity Relationships", *J. of Pharmaceutical Sciences*, 72, 5, (1983),538–541.

Shcherbakova, I. V., et al., "2–Benzopyrilium salts.35.Synthesis of the natural alkaloid dehydronorcoralydine and other substituted salts of dibenzo a,g quinolizine", *Chemical Abstracts*, 112 (19), Abstract No. 179554,(May 7, 1990),pp. 75–80.

Singh, Malvinder P., et al., "Synthesis and Sequence–Specific DNA Binding of a Topoisomerase Inhibitory Analog of Hoechst 33258 Designed for Altered Base and Sequence Recognition", *Chem. Res. Toxicol.*, 5, (1992),pp. 597–607.

Sotomayor, N. , et al., "Oxidation reactions of 2'–functionalized 3–aryltetrahydro–and 3,4–dihydroisoquinolines", *Chemical Abstracts*, 124 (11), Abstract No. 145854,(Mar. 11, 1996),p. 1227.

Stermitz, Frank R., et al., "Synthesis and Biological Activity of Some Antitumor Benzophenanthridinum Salts", *Journal of Medicinal Chemistry*, 18, 1975,pp. 708–713.

Sun, et al., *Chemical Abstracts*, 123 (15), Abstract No. 198740r,(1995), 1 p.

Sun, Qun , et al., "Structure activity of novel topoisomerase I inhibitors related to Hoechst 33342", *Abstract 6—Proceedings of the American Association of Pharmaceutical Scientists Eastern Regional Meeting*, Hyatt Regency Hotel, New Brunswick, NJ,(Jun. 5–6, 1995),p. 25.

Sun, Qun, et al., "Structure Activity of Topoisomerase I Poisons Related to Hoechst 33342", *Bioorganic & Medicinal Chemistry Letters, 4 (24)*, (1994),pp. 2871–2876.

Sun, Qun, et al., "Structure–activity studies related to minor groove–binding ligands which inhibit mammalian DNA topoisomerase I", *Cancer Institute of New Jersey's First Annual Scientific Retreat, Abstract 2*, Princeton Marriott Forrestal Village, Princeton, NJ,(Jun. 7, 1994),p. 66.

Sun, Qun, et al., "Synthesis and Evaluation of Terbenzimidazoles as Topoisomerase I Inhibitors", *J. Med. Chem*, vol. 38,(1995),pp. 3638–3644.

Sun, Q., et al., "Synthesis and Pharmacological Evaluation of a Series of Novel DNA Topoisomerase I Inhibitors as Antitumor Agents", *Scientific Proceedings of 86th Annual Meeting of the American Association for Cancer Research, Abstract 3*, Toronto, Canada,(Mar. 18–22, 1995),1 p.

Sun, Qun, et al., "Synthesis and pharmacological evaluation of a series of novel DNA topoisomerase I inhibitors as antitumor agents", *Proceedings of the 86th Annual Meeting of the American Association for Cancer Research*, Toronto, Ontario, Canada,(1995),p. 2688.

Sun, Qun, et al., "Synthesis of Benzimidazo[2,1–a]isoquinolines and 5,6–Dihydrobenzimidazo[2,1–a]isoquinolines", *Syn. Lett., submitted*, Paper No. 7,(1995),6 p.

Walterova, D., et al., "Isolation, Chemistry and Biology of Alkaloids from plants of Papaveraceae. Part XCV. Practical application of isotachophoresis in analysis of isoquinoline alkaloids", *Chemical Abstract, 104 (12)*, (1986),pp. 23–36.

Wang, Li–Kai, et al., "Inhibition of Topoisomerase I Function by Coralyne and 5,6 –Dihydrocoralyne", *Chem. Res. Toxicol., 9*, (1996),pp. 75–83.

Wang, Li–Kai, et al., "Inhibition of Topoisomerase I Function by Nitidine and Fagaronine", *Chem. Res. Toxicol., 6*, (1993),pp. 813–818.

Waters, W. A., et al., "Reactions of Free Benzyl Radicals with Benz[a]– and Benz[c]acridine", *Chemical Abstracts, 54*, Abstract, Column 3424b, (1960), 1 p.

Yadagiri, Bathini, et al., "Convenient Routes to Substituted Benzimidazoles and Imidazolo[4,5–b]Pyridines Using Nitrobenzene as Oxidant", *Synthetic Communications, 20 (7)*, (1990),pp. 955–963.

Yamamoto, Y., et al., "Reaction of 6H–1, 3–oxazin–6–one with benzyne giving isoquinoline derivatives", *Chemical Abstracts, 118 (7)*, Abstract No. 059563,(Feb. 15, 1993),2 p.

Yamashita, Yoshinori, et al., "Induction of Mammalian DNA Topoisomerase I and II Mediated DNA Cleavage by Saintopin, a New Antitumor Agent from Fungus", *Biochemistry, 30*, (1991),pp. 5838–5845.

Yamashita, Yoshinori, et al., "Induction of Mammalian DNA Topoisomerase I Mediated DNA Cleavage by Antitumor Indolocarbazole Derivatives", *Biochemistry, 31*, (1992), pp. 12069–12075.

\* cited by examiner (Intermediate 1)

(Intermediate 2)

CPT = Camptothecin

Hoechst 33342

BZ-III-26  DL-II-91

HETEROCYCLIC CYTOTOXIC AGENTS

CROSS-REFERENCE TO RELATED APPLICATIONS

This application is a continuation under 35 USC 111(a) of PCT/US00/29583 filed Oct. 26, 2000 (WO 01/32631 A3), which claimed priority from U.S. Provisional Patent Application Serial No. 60/162,540, filed Oct. 29, 1999, which applications are incorporated by reference.

GOVERNMENT FUNDING

The invention described herein was made with U.S. Government support under grant number CA39662 awarded by the National Cancer Institute. The United States Government has certain rights in the invention.

BACKGROUND OF THE INVENTION

DNA-topoisomerases are enzymes which are present in the nuclei of cells where they catalyze the breaking and rejoining of DNA strands, which control the topological state of DNA. Recent studies also suggest that topoisomerases are also involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents which are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin). In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., *Cancer Res.* 1993, 53, 1332–1335; Sun et al., *J. Med. Chem.* 1995, 38, 3638–3644; Kim et al., *J. Med. Chem.* 1996, 39, 992–998), certain benzo[c]phenanthridine and protoberberine alkaloids and their synthetic analogs (Makhey et al., *Med. Chem. Res.* 1995, 5, 1–12; Janin et al., *J. Med. Chem* 1975, 18, 708–713; Makhey et al., *Bioorg. & Med. Chem.* 1996, 4, 781–791), as well as the fungal metabolites, bulgarein (Fujii et al., *J. Biol. Chem.* 1993, 268, 13160–13165) and saintopin (Yamashita et al., *Biochemistry* 1991, 30, 5838–5845) and indolocarbazoles (Yamashita et al., *Biochemistry* 1992, 31, 12069–12075) have been identified as topoisomerase I poisons.

The exceptional topoisomerase poisoning observed with coralyne, nitidine, 5,6-dihydro-8-desmethylcoralyne and related analogs prompted several recent studies on those structural features which are associated with their ability to act specifically as poisons of topoisomerase I or topoisomerase II (Gatto et al., *Cancer Res.* 1996, 56, 2795–2800; Wang et al., *Chem. Res. Toxicol.* 1996, 9, 75–83; Wang et al., *Chem. Res. Toxicol.*, 1993, 6, 813–818). A common feature associated with all three of these agents is the presence of a 3-phenylisoquinolinium moiety within their structure.

Despite the observation that several of these compounds had similar potency to camptothecin as a topoisomerase I poison or similar potency to VM-26 as a topoisomerase II poison, they possessed only modest cytotoxic activity. The absence of a more direct correlation with their potency as topoisomerase poisons was attributed, in part, to the likelihood that these agents are not likely to be absorbed as effectively into cells as either camptothecin or VM-26. The presence of the quaternary ammonium group most likely impedes cellular uptake. It has been speculated that agents such as coralyne and nitidine may need to undergo hydrolysis to permit effective transport, with subsequent dehydration or cyclodehydration to reform the quaternary ammonium parent compound. This may explain the relatively poor antitumor activity observed in vivo with agents such as coralyne or nitidine.

Presently, a need exists for additional agents that are useful for treating cancer.

SUMMARY OF THE INVENTION

Applicant has discovered compounds that show inhibitory activity against topoisomerase I and/or topoisomerase II, and compounds that are effective cytotoxic agents against cancer cells, including drug-resistant cancer cells. Accordingly, the invention provides a compound of the invention which is a compound of formula I:

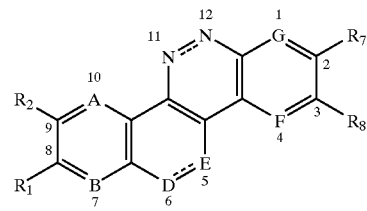

wherein:

A is N or $CR_3$;

B is N or $CR_s$;

D is $NR_e$ or $CR_aR_b$;

E is $NR_f$ or $CR_cR_d$;

F is N or $CR_i$;

G is N or $CR_6$;

$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$, are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$ alkyl if the bond between the 11- and 12-positions represented by—is absent; or $R_a$ is hydrogen or $(C_1-C_6)$alkyl and $R_b$ is absent if the bond between the 11- and 12-positions represented by—is present;

$R_c$ and $R_d$ are each independently hydrogen or $(C_1-C_6)$ alkyl if the bond between the 11- and 12-positions represented by—is absent; or $R_c$ is hydrogen or $(C_1-C_6)$alkyl and $R_d$ is absent if the bond between the 11- and 12-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1C_6)$alkoxy, or $(C_1-C_6)$alkanoyl; or $R_n$ and $R_p$ together with the nitrogen to which they are attached are pyrrolidino, piperidino, morpholino, or thiomorpholino;

wherein any aryl is optionally be substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$ alkoxy;

provided no more than two of A–G comprise nitrogen; or a pharmaceutically acceptable salt thereof.

The invention also provides a pharmaceutical composition comprising a effective amount of a compound of formula I, or a pharmaceutically acceptable salt thereof, in combination with a pharmaceutically acceptable diluent or carrier.

The invention also provides a method of inhibiting cancer cell growth, comprising administering to a mammal afflicted with cancer, an amount of a compound of formula (I), effective to inhibit the growth of said cancer cells.

The invention also provides a method comprising inhibiting cancer cell growth by contacting said cancer cell in vitro or in vivo with an amount of a compound of claim 1, effective to inhibit the growth of said cancer cell.

The invention also provides a compound of formula I for use in medical therapy (preferably for use in treating cancer, e.g. solid tumors), as well as the use of a compound of formula I for the manufacture of a medicament useful for the treatment of cancer, e.g. solid tumors.

The invention also provides processes and novel intermediates disclosed herein which are useful for preparing compounds of the invention. Some of the compounds of formula I are useful to prepare other compounds of formula I.

K. W. Gopinath et al., *Indian J. Chem.*, 1958, 504–509, disclose the preparation of 2,3,8,9-tetramethoxy-5,6-diazachrysene and 2,3-8,9-bismethylenedioxy-5,6-diazacrysene. Accordingly, the compounds of the invention may preferably exclude the compounds 2,3,8,9-tetramethoxy-5,6-diazachrysene and 2,3-8,9-bismethylenedioxy-5,6-diazacrysene.

The compounds of the invention may also preferably exclude compounds of formula (I) wherein D is $NR_e$; when A $CR_3$; B is $CR_s$; E is $CR_cR_d$; F is $CR_f$; and G is $CR_6$.

The compounds of the invention may also preferably exclude compounds wherein $R_1-R_3$ and $R_6-R_8$ are each hydrogen.

The compounds of the invention may also preferably exclude 9-hydroxy-2,3,8-trimethoxydibenzo[c,h]cinnoline.

Preferably, for a compound of formula I one of $R_2$ and $R_8$ is hydrogen, methyl, nitro, hydroxy, amino, fluoro or chloro; or at least one of $R_2$ and $R_8$ forms part of a methylenedioxy.

DETAILED DESCRIPTION

Figure 1:
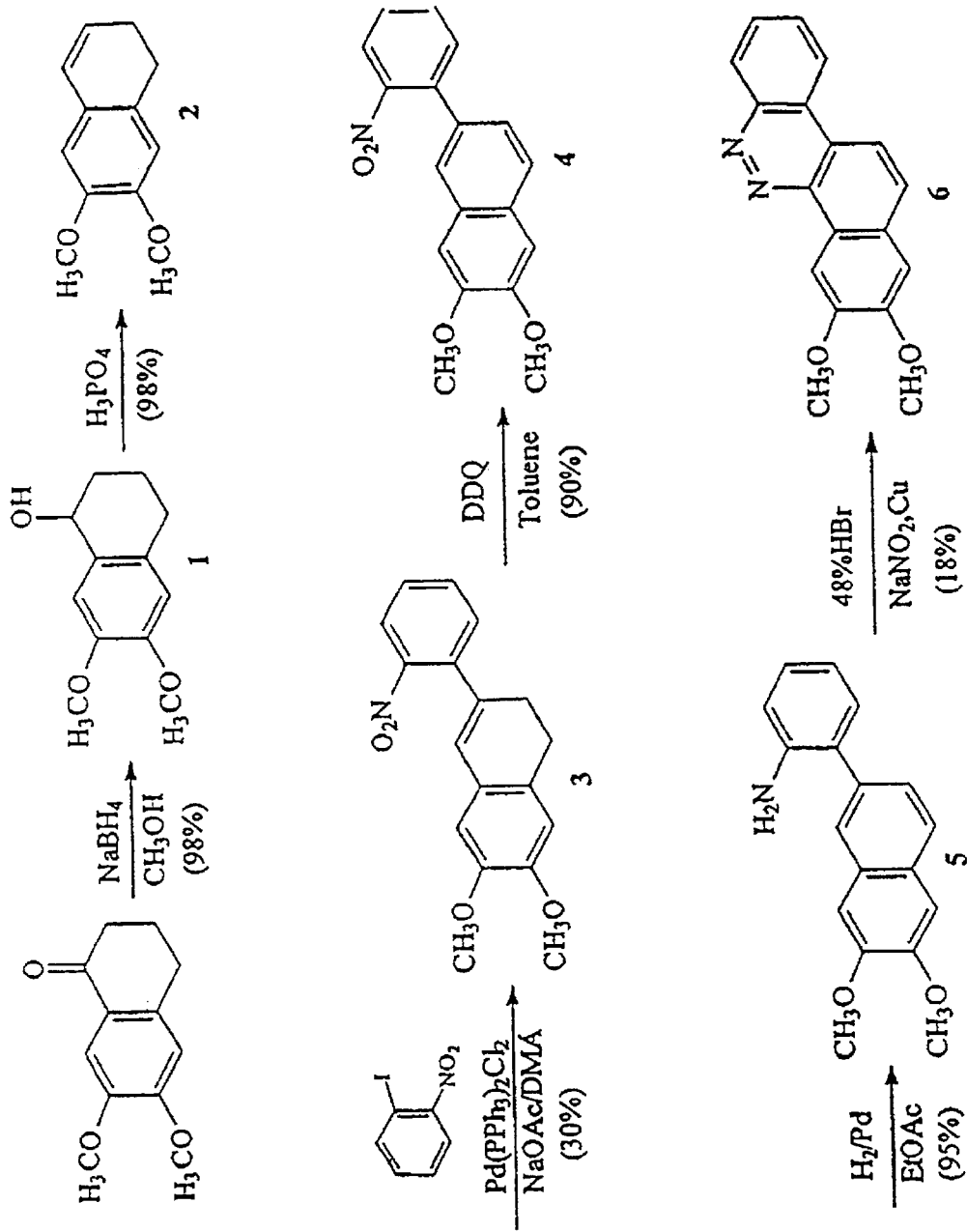
FIGS. 1–5: illustrate the synthesis of compounds of the invention.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl, butanoyl, pentanoyl, or hexanoyl; and aryl can be phenyl, indenyl, or naphthyl;.

Specifically, $R_2$ or $R_7$ can be hydroxy, methoxy, benzyloxy, amino, hydroxymethyl, aminomethyl, aminocarbonyl, methoxycarbonyl, trifluoromethyl, 3-aminopropoxycarbonyl, or 2-hydroxyethyl.

Specifically, $R_3$ can be hydrogen.

Specifically, $R_s$ and $R_t$ are each hydrogen.

A specific group of compounds are compounds of formula I:

[Chemical structure diagram with positions labeled 1-12 showing rings A, B with substituents R1, R2, and ring containing R7, R8, with atoms/groups A, B, D, E, F, G and N at position 12]

wherein:
A is N or $CR_3$;
B is N or $CR_s$;
D is $NR_e$ or $CR_aR_b$;
E is $NR_f$ or $CR_cR_d$;
F is N or $CR_t$;
G is N or $CR_6$;
$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;
$R_6$, $R_7$ and $R_8$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;
each bond represented by—is individually present or absent;
$R_a$ and $R_b$ are each independently hydrogen or $(C_1-C_6)$alkyl if the bond between the 11- and 12-positions represented by—is absent; or $R_a$ is hydrogen or $(C_1-C_6)$alkyl and $R_b$ is absent if the bond between the 11- and 12-positions represented by—is present;
$R_c$ and $R_d$ are each independently hydrogen or $(C_1-C_6)$alkyl if the bond between the 11- and 12-positions represented by—is absent; or $R_c$ is hydrogen or $(C_1-C_6)$alkyl and $R_d$ is absent if the bond between the 11- and 12-positions represented by—is present;
$R_e$ is hydrogen or $(C_1-C_6)$alkyl if the bond between the 5- and 6-positions represented by—is absent; or $R_e$ is absent if the bond between the 5- and 6-positions represented by—is present;
$R_f$ is hydrogen or $(C_1-C_6)$alkyl if the bond between the 5- and 6-positions represented by—is absent; or $R_f$ is absent if the bond between the 5- and 6-positions represented by—is present;
each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and
each $R_m$ is independently $(C_1-C_6)$alkanoyl, aryl, or aryl $(C_1-C_6)$alkyl;
each $R_s$ and $R_t$ is independently hydrogen, methyl, nitro, hydroxy, amino, or halo;
wherein any $(C_1-C_6)$alkyl, $(C_3-C_6)$cycloalkyl, or $(C_1-C_6)$ alkoxy of $R^1$, $R^2$, $R^3$ $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;
wherein any aryl is optionally be substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$ alkoxy;
provided no more than two of A–G comprise nitrogen; and
provided at least one of $R_2$ and $R_8$ is hydrogen, methyl, nitro, hydroxy, amino, fluoro or chloro; or at least one of $R_2$ and $R_8$ forms part of a methylenedioxy;
or a pharmaceutically acceptable salt thereof. Preferably, within this specific group of compounds the compound of formula I is not 2,3-8,9-bismethylenedioxy-5,6-diazacrysene; and $R_1$–$R_3$ and $R_6$–$R_8$ are not each hydrogen.

A specific group of compounds are compounds of formula I wherein $R_1$, $R_2$ and $R_3$ are each individually hydrogen, or $(C_1-C_6)$alkoxy; or $R_1$ and $R_2$ taken together are methylenedioxy (—$OCH_2O$—) and $R_3$ is hydrogen or $(C_1-C_6)$alkoxy; or a pharmaceutically acceptable salt thereof.

Another specific group of compounds are compounds of formula I wherein $R_7$ or $R_8$ is $(C_1-C_6)$alkoxy; or $R_7$ and $R_8$ taken together are methylenedioxy; or a pharmaceutically acceptable salt thereof.

Another specific group of compounds are compounds of formula I wherein $R_7$ and $R_8$ taken together are methylenedioxy; or a pharmaceutically acceptable salt thereof.

Another specific group of compounds are compounds of formula I wherein the bonds represented by—are both present; or a pharmaceutically acceptable salt thereof.

Another specific group of compounds are compounds of formula I wherein the bond between the 5- and the 6-positions that is represented by—is absent; or a pharmaceutically acceptable salt thereof.

Another specific group of compounds are compounds of formula I wherein the bond between the 11- and the 12-positions that is represented by—is absent; or a pharmaceutically acceptable salt thereof.

Another specific group of compounds are compounds of formula I wherein the bonds represented by—are both absent; or a pharmaceutically acceptable salt thereof.

Figure 6:
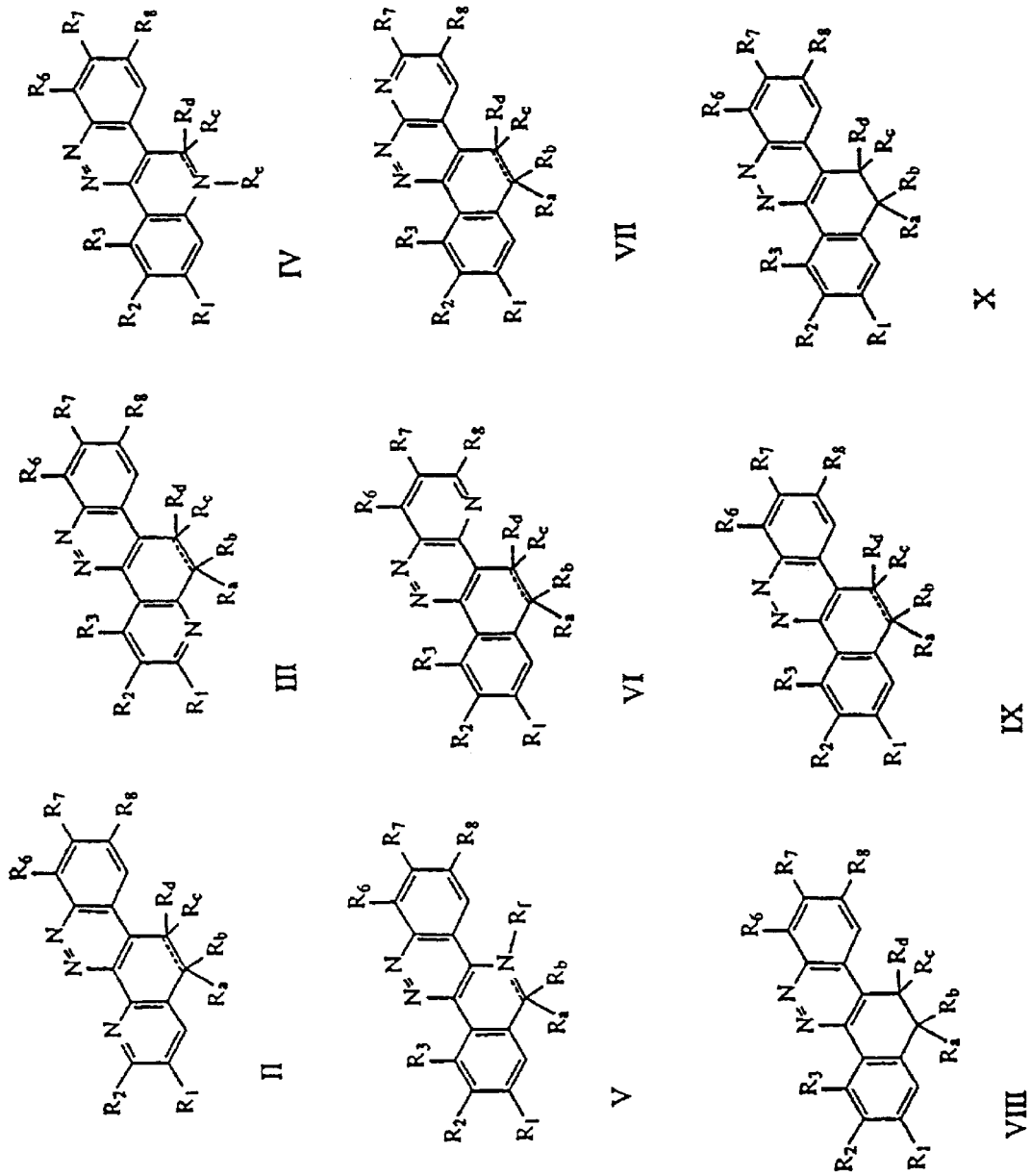
FIG. 6: illustrates specific compounds of Formula I.
Figure 7:
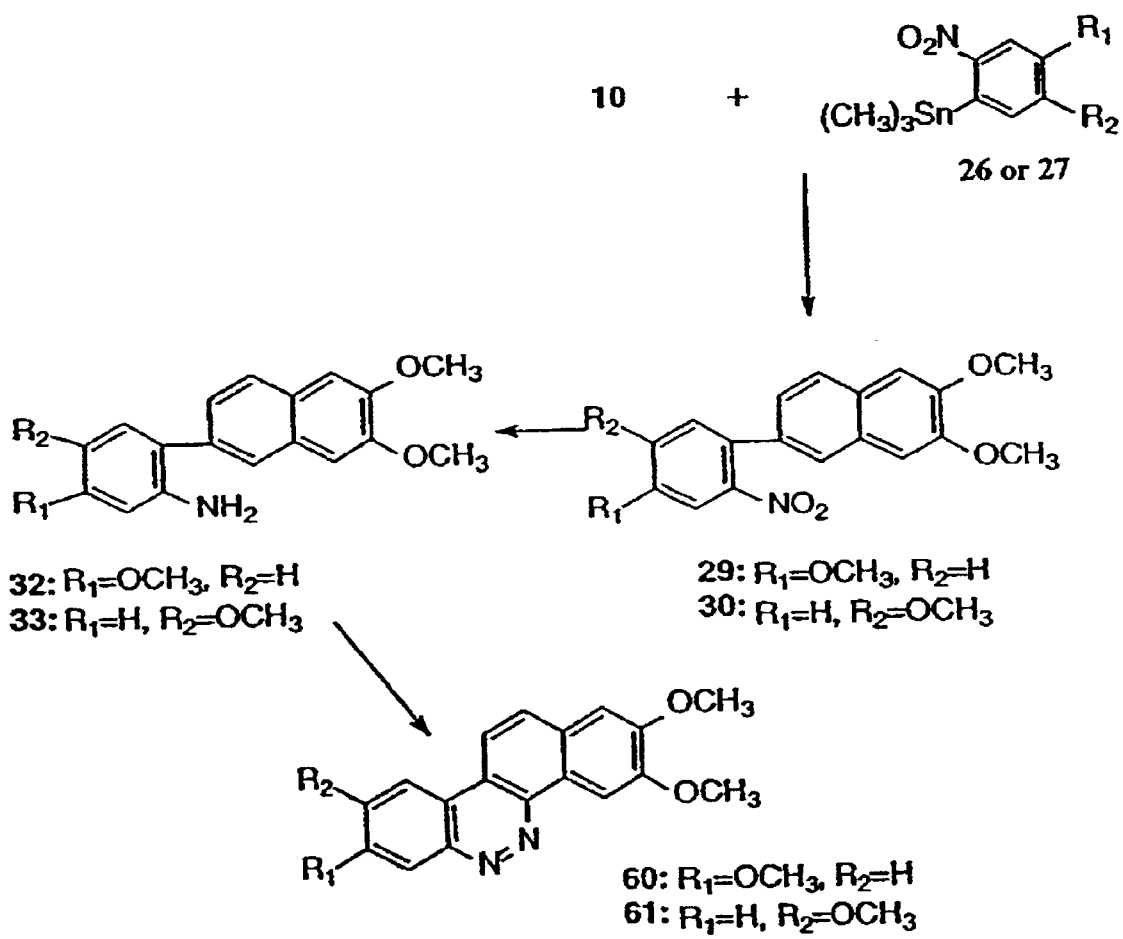
FIGS. 7–10: illustrate the synthesis of compounds of the invention.
Figure 8:
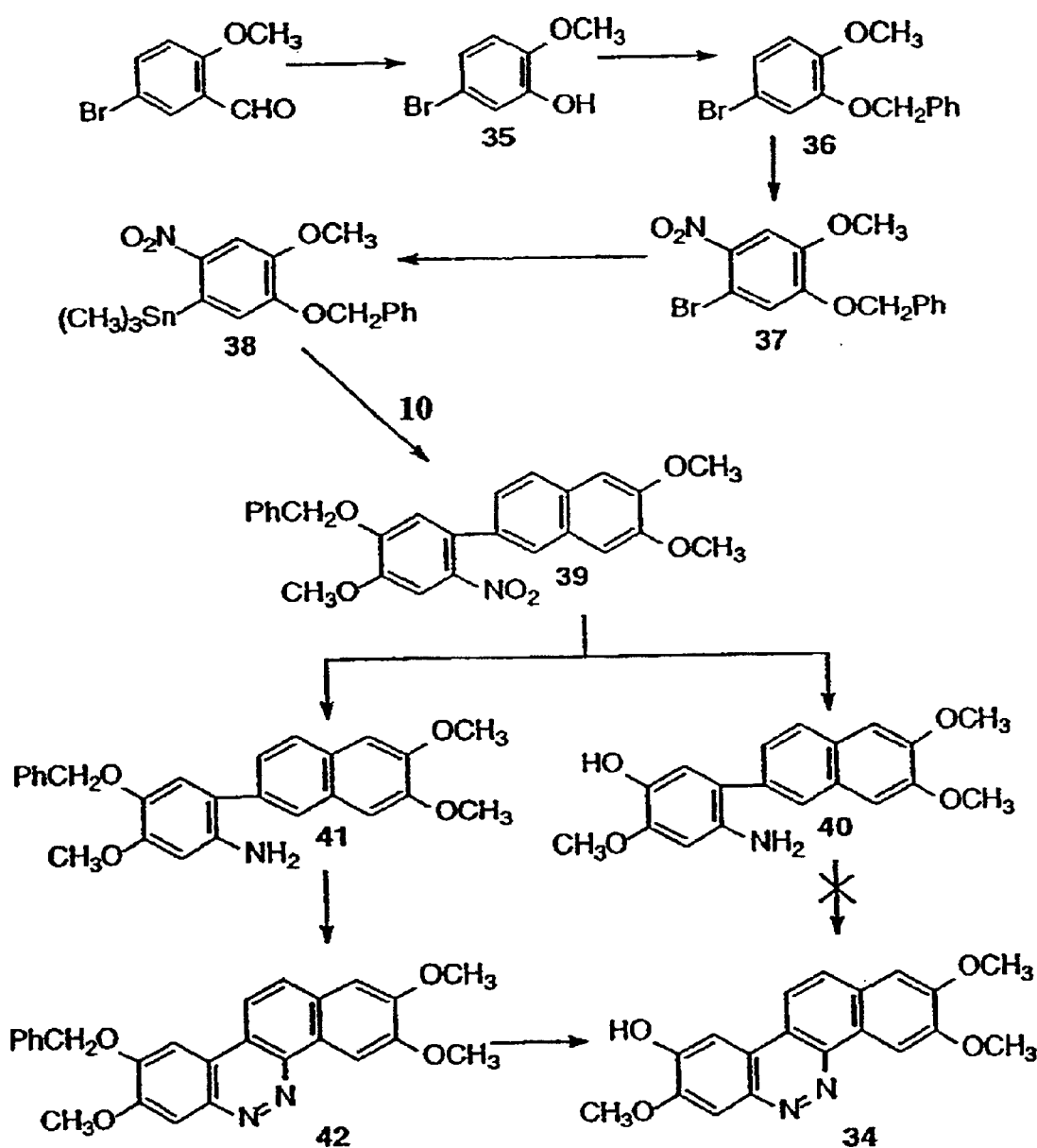
Figure 9:
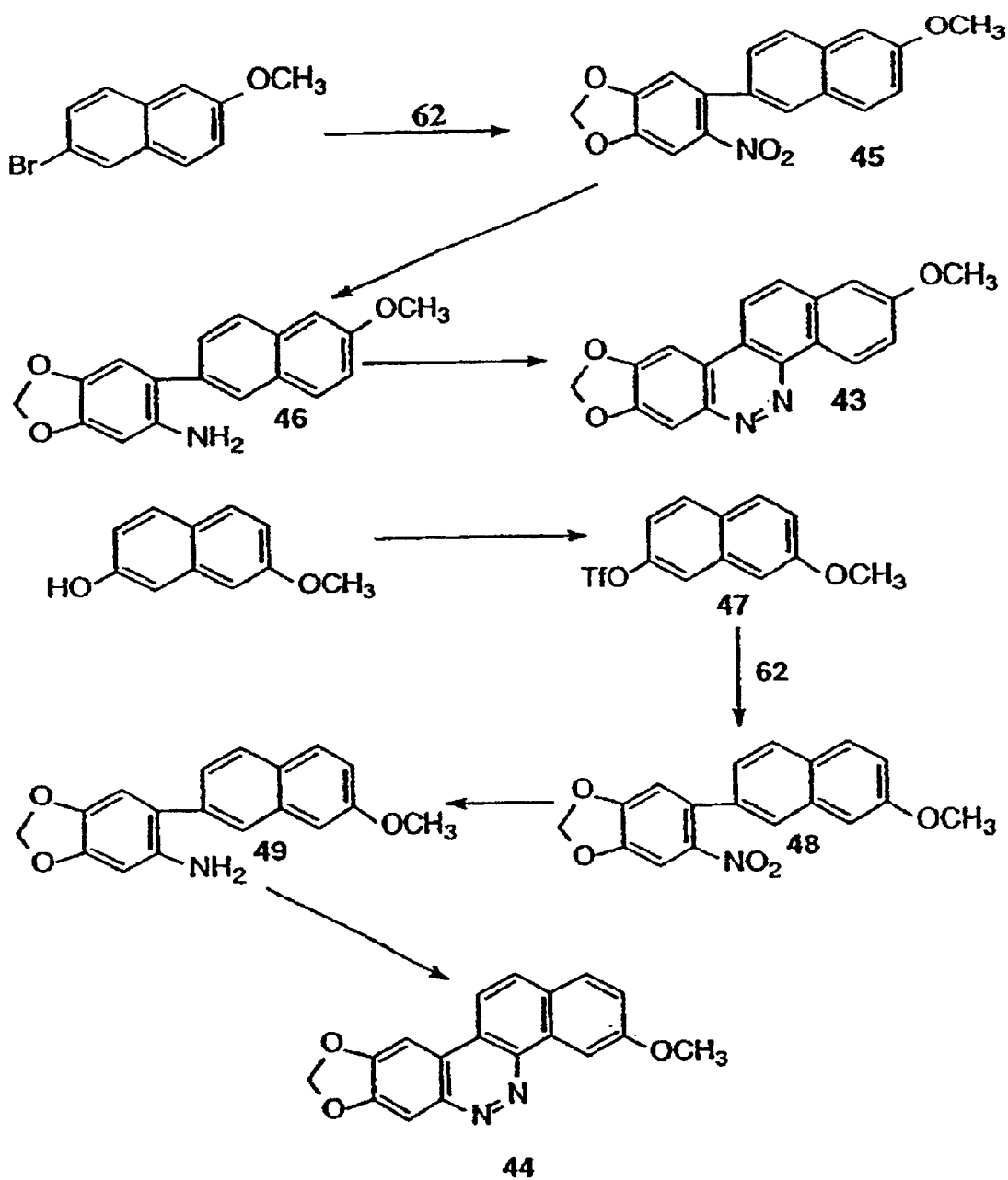
Figure 10:
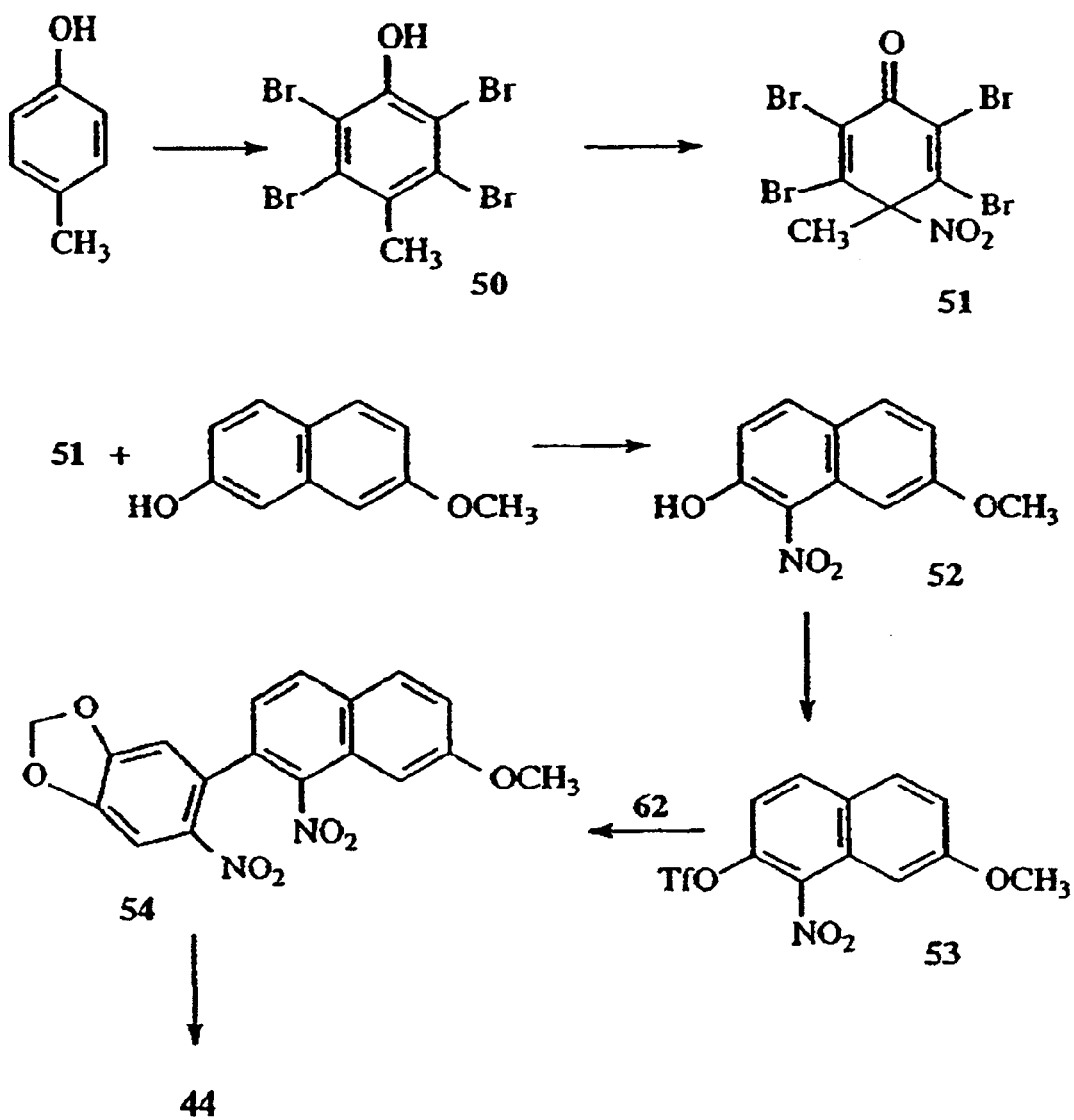

A specific compound of formula I is a compound of formula II, III, IV, V, VI, VII, VIII, IX or X (FIG. 6) wherein $R_1$–$R_8$, $R_a$–$R_t$ have any of the values, specific values or preferred values described herein for a compound of formula I. Compounds of formulae II–X can be prepared from available starting materials using procedures known in the art, or using procedures analogous to those described herein.

A compound of formula I can be prepared by subjecting an intermediate of formula XX (wherein $R_1$–$R_8$ and A–G have any of the values, specific values, or preferred values described herein for a corresponding substituent in a compound of formula I):

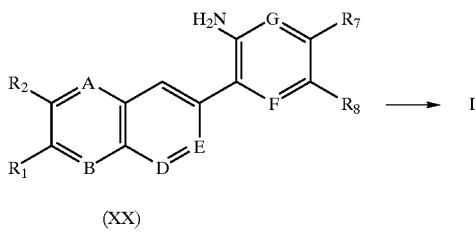

(XX)

to conditions suitable for formation of the tetracyclic ring system. Conditions suitable for formation of the tetracyclic ring system are well known to the art. For example, see Example 1 hereinbelow.

An intermediate of formula XX can be prepared from readily available starting materials using procedures that are known in the art, or can be prepared using the procedures described hereinbelow, which are illustrated in the figures.

As illustrated in FIG. 1 and as shown in Example 1, reduction of 6,7-dimethoxy-1-oxo-1,2,3,4-tetrahydronaphthlene, provides an alcohol 1, which can be dehydrated to provide dihydronaphthlene 2. Coupling with an 2-iodo-nitrobenzene provides 3 which can be oxidized to provide 4. Reduction of the nitro group provides amine 5, which is a compound of formula XX.

Figure 2:
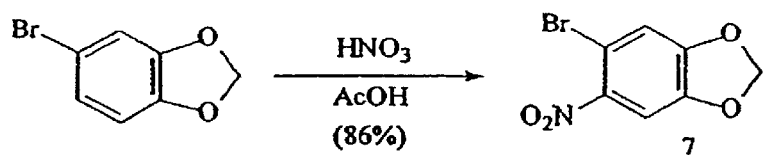
Figure 2:
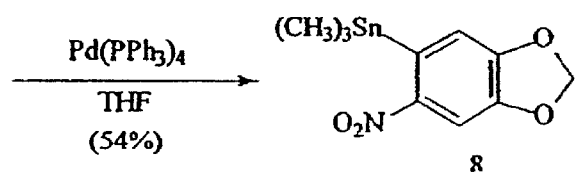
Figure 2:
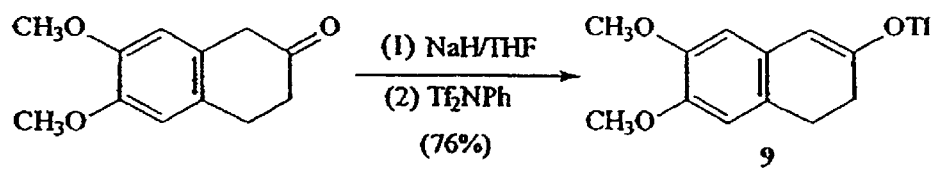
Figure 2:
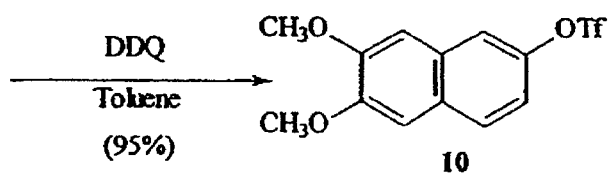
Figure 3:
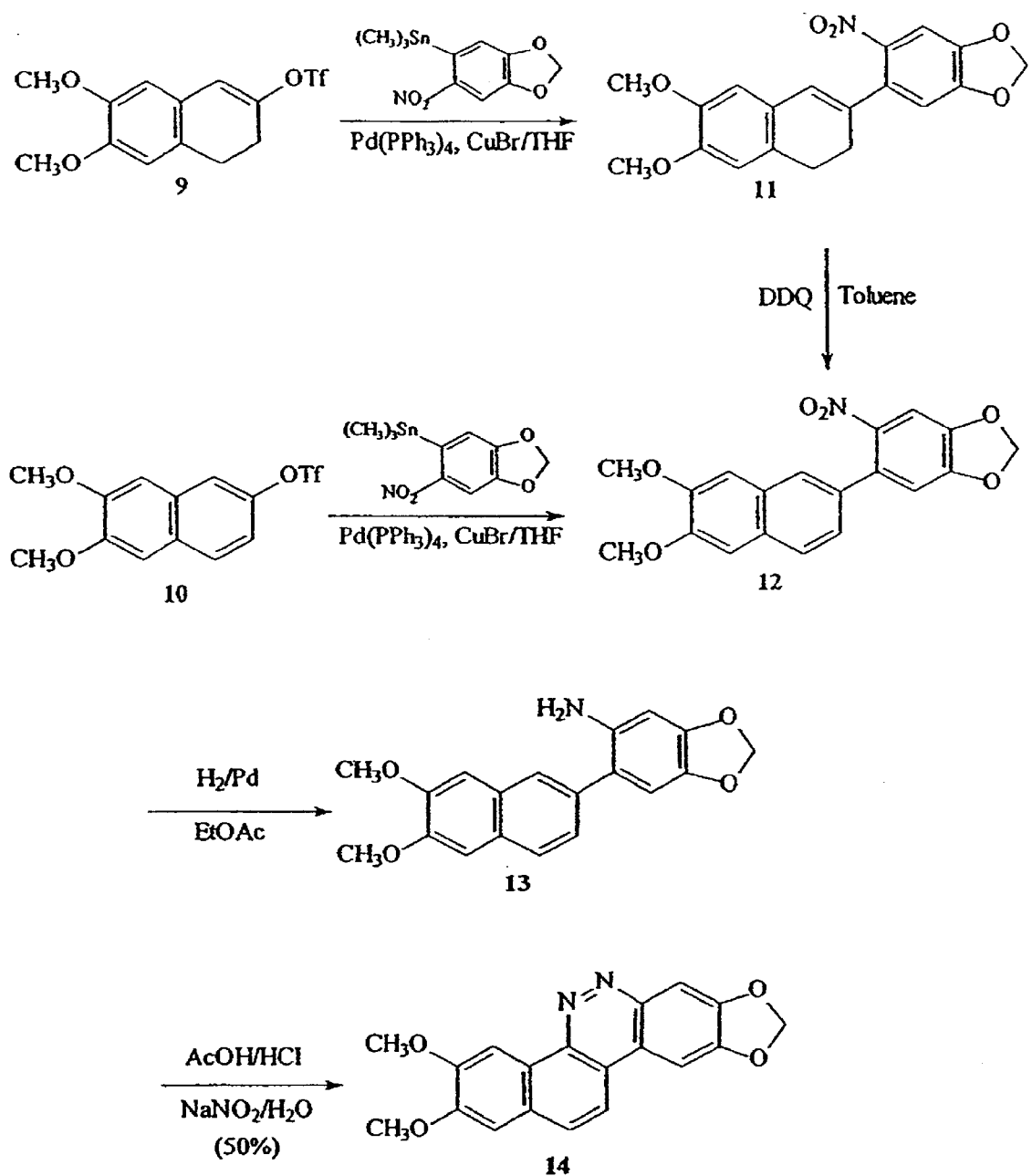
Figure 4:
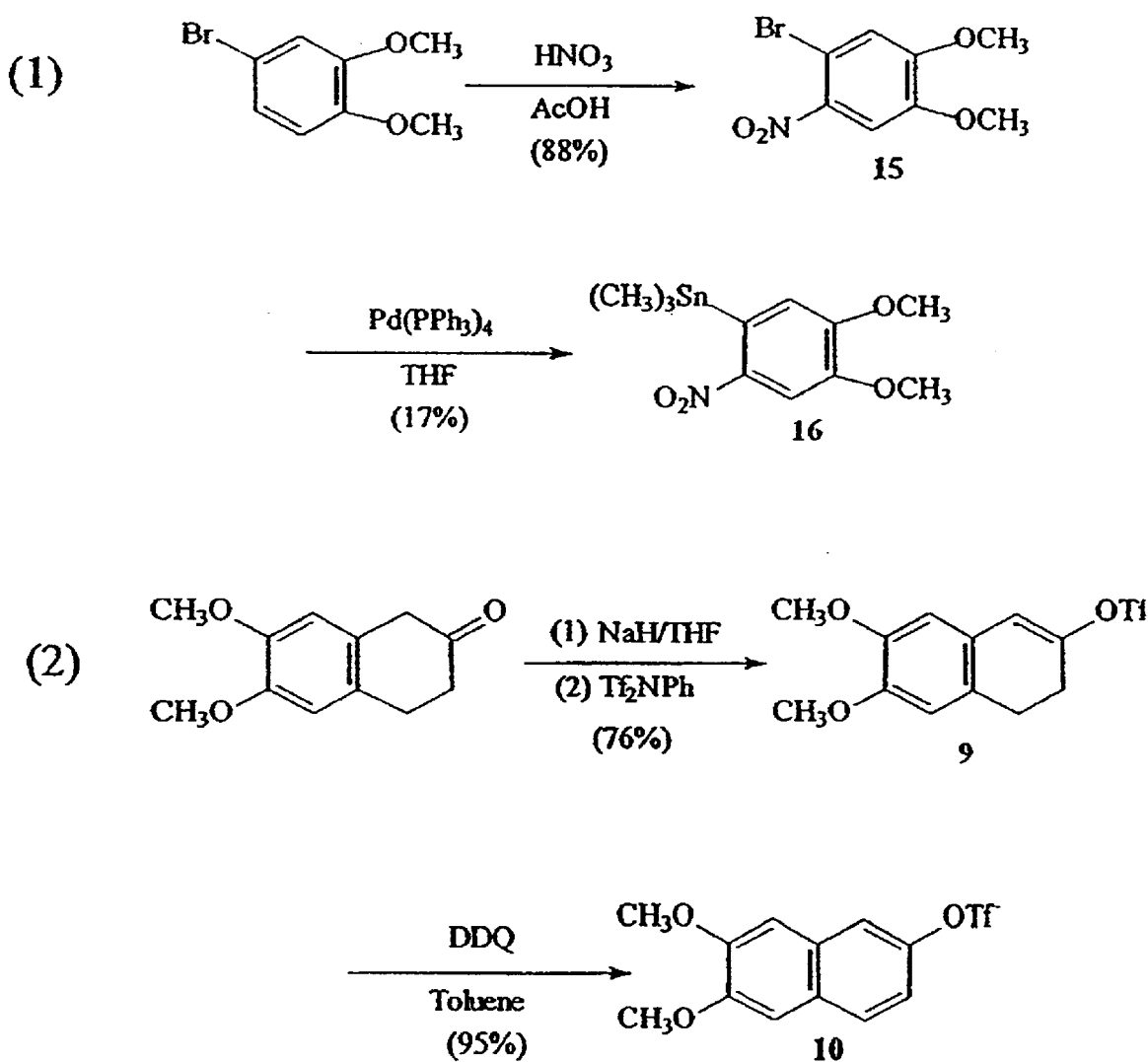

As illustrated in FIGS. 2, 3, and 4, and as shown in Example 2, nitration of 4-bromoveratrole under standard conditions provides nitro compound 7, which can be converted to stannane 8 under standard conditions. Coupling of stannane 8 with triflate 9 provides 11, which can be oxidized to provide 12. Alternatively, stannane 8 can be coupled with triflate 10 to provide 12. Reduction of the nitro group in 12 under standard conditions, provides an intermediate of formula XX. As illustrated in FIG. 4, triflate 9 can be prepared from 6,7-dimethoxy-2-oxo-1,2,3,4-tetrahydronaphthlene by formation of the eneoltriflate, under standard conditions. Triflate 10 can be prepared from 9 by oxidation under standard conditions.

Figure 5:
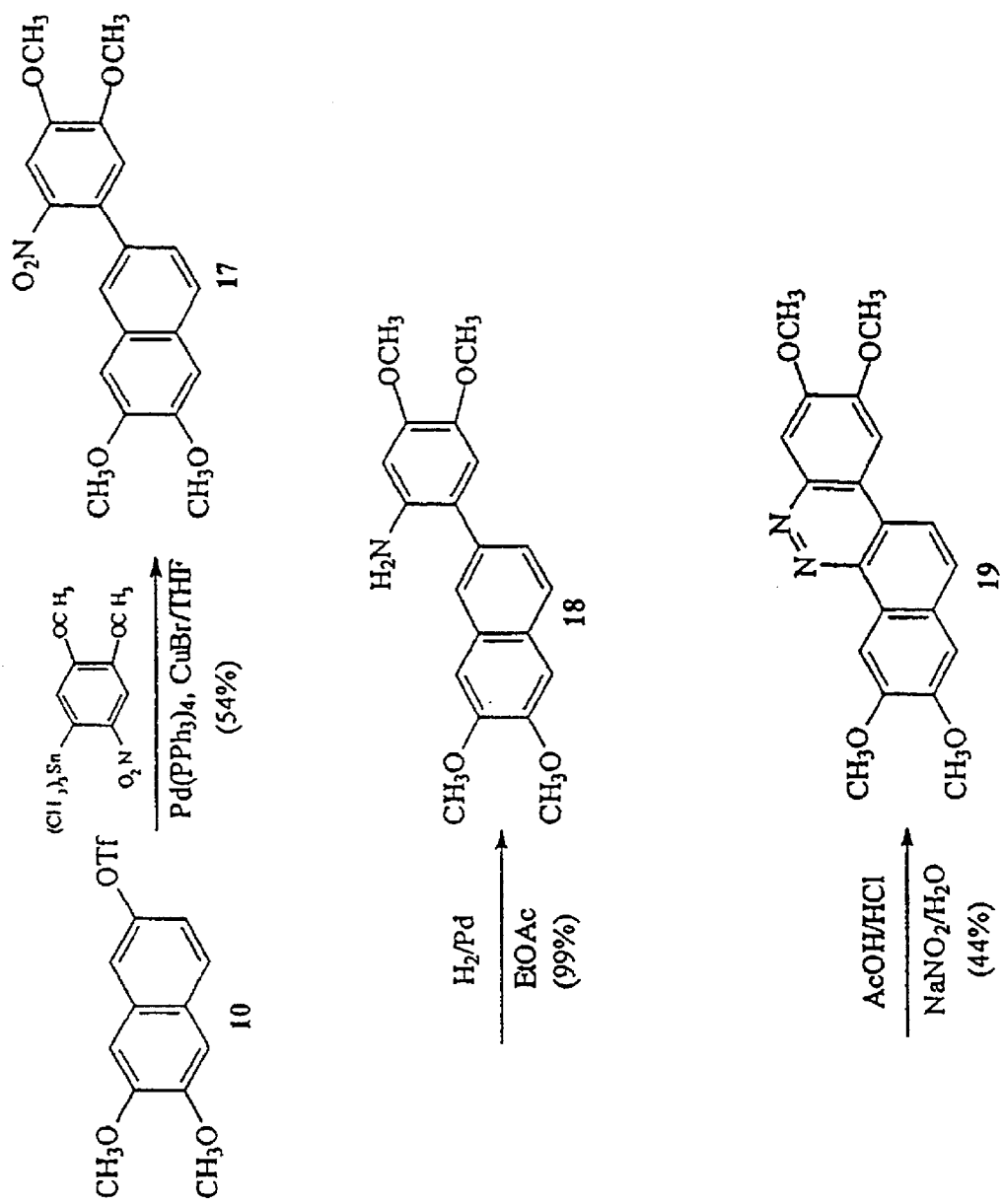

As illustrated in FIGS. 4 and 5, and as shown in Example 3, an intermediate 16 can be prepared by nitration of readily available 3,4-dimethoxybromobenzene under standard conditions, followed by formation of the corresponding stannane 16. Coupling of triflate 10 and stannane 16 under standard conditions, provides nitro compound 17 which can be reduced to provide an intermediate of formula XX.

Other intermediates of formula XX can be prepared using procedures similar to those described herein by selecting appropriate starting materials to provide the desired intermediate of formula XX.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I or II mediated DNA cleavage can be determined using pharmacological models that are well known to the art, for example, using a model like Test A described below.

Test A. Topoisomerase I-mediated DNA Cleavage Assay

Human topoisomerase I was expressed in *E. Coli* and isolated as a recombinant fusion protein using a T7 expression system as described previously (Makhey, D. et al., *Bioorg. Med. Chem.*, 2000, 8, 1–11). DNA topoisomerase I was purified from calf thymus gland as reported previously (Maniatis, T., et al., J. Molecular Cloning, a Laboratory Manual, Cold Spring Harbor Laboratory, Cold Spring Harbor, N.Y., 149–185). Plasmid YepG was also purified by the alkali lysis method followed by phenol deproteination and CsCl/ethidium isopycnic centrifugation method as described (Maniatis, T.; Fritsch, E. F.; Sambrook, J. *Molecular Cloning, a Laboratory Manual*; Cold Spring Harbor Laboratory: Cold Spring Harbor, N.Y. 1982; pp 149–185) .[102] The end-labeling of the plasmid was accomplished by digestion with a restriction enzyme followed by end-filling with Klenow polymerase as previously described (Liu, L. F.; Rowe, T. C.; Yang, L.; Tewey, K. M.; Chen, G. L. "Cleavage of DNA by mammalian topoisomerase II," *J Biol. Chem.* 1983, 258, 15365).[103] Cleavage assays were performed as previously reported (B. Gatto et al. *Cancer Res.*, 1996, 56, 2795–2800).[13] The drug and the DNA in presence of topoisomerase I was incubated for 30 minutes at 37° C. After development of the gels, typically 24-hour exposure was used to obtain autoradiograms outlining the extent of DNA fragmentation. Topoisomerase I-mediated DNA cleavage values are reported as REC, Relative Effective Concentration, i.e. concentrations relative to 2,3-dimethoxy-8,9-methylenedioxybenzo[i]phenanthridine, whose value is arbitrarily assumed as 1.0, that are able to produce the same cleavage on the plasmid DNA in the presence of human topoisomerase I. Relative potency was based upon the relative amount of drug needed to induce approximately 10% DNA fragmentation. Assays were performed under the direction of Dr. L. F. Liu, Department of Pharmacology, The University of Medicine and Dentistry of New Jersey, Robert Wood Johnson Medical School, Piscataway, N.J. Data from Test A for representative compounds of the invention is shown in Table 1.

TABLE 1

| Compound | Topoisomerase I-mediated DNA cleavage |
| --- | --- |
| 6 | 5 |
| 14 | 0.01 |
| 19 | >100 |
| 60 | 2 |
| 61 | 10 |

The cytotoxic effects of a compound of the invention can be determined using pharmacological models that are well known to the art, for example, using a model like Test B described below.

Test B. Inhibition of Cell Growth: MTT-microtiter Plate Tetrazolinium Cytotoxicity Assay (RPMI 8402, CPT-K5, U937, U937/CR Cells)

The cytotoxicity was determined using the MTT-microtiter plate tetrazolinium cytotoxicity assay (MTA) (See Chen A. Y. et al. *Cancer Res.* 1993, 53, 1332; Mosmann, T. J., *J. Immunol. Methods* 1983, 65, 55; and Carmichael, J. et al. *Cancer Res.* 1987, 47, 936). The human lymphoblast RPMI 8402 and its camptothecin-resistant variant cell line, CPT-K5 were provided by Dr. Toshiwo Andoh (Anchi Cancer Research Institute, Nagoya, Japan) (see Andoh, T.; Okada, K. "Drug resistance mechanisms of topoisomerase I drugs," *Adv. in Pharmacology* 1994, 29B, 93). Human U-937 myeloid leukemia cells and U-937/CR cells were described by Rubin et al., *J. Biol. Chem.*, 269, 2433–2439 (1994). The cytotoxicity assay was performed by using 96-well microtiter plates using 2000 cells/well, in 200 mL of growth medium. Cells were grown in suspension at 37° C. in 5% $CO_2$ and maintained by regular passage in RPMI medium supplemented with 10% heat-inactivated fetal bovine serum, L-glutamine (2 mM), penicillin (100U/mL), and streptomycin (0.1 mg/mL). For determination of $IC_{50}$, cells were exposed continuously for 3–4 days to varying concentrations of drug, and MTT assays were performed at the end of the fourth day. Each assay was performed with a control that did not contain any drug. All assays were performed at least twice in 6 replicate wells. All assays were performed under the direction of Dr. L. F. Liu, Department of Pharmacology, The University of Medicine and Dentistry of New Jersey, Robert Wood Johnson Medical School, Piscataway, N.J. Representative data is shown in Tables 2 and 3.

TABLE 3

| [] $\mu M$ | RPMI 8402 | CPT-K5 | U937 | U937/CR |
| --- | --- | --- | --- | --- |
| Bz-III-26* | 0.5 | 0.3 | 0.09 | 0.06 |
| DL-II-91* | 0.3 | 0.13 | 0.03 | 0.025 |
| 6 | 3 | 10 | 3 | 3 |
| 14 | 0.06 | 6 | 0.06 | 3 |
| 19 | 10 | >10 | 10 | 20 |
| 60 | 2 | 4 | 1.9 | 2.5 |
| 61 | 4 | 31 | 3 | 6 |
| 34 | >100 | >100 | >100 | >100 |
| 42 | 38 | 61 | >100 | 40 |
| 43 | >100 | 52 | 38 | 30 |
| 44 | 0.5 | 1.3 | 43 | 0.9 |

Figure 11:
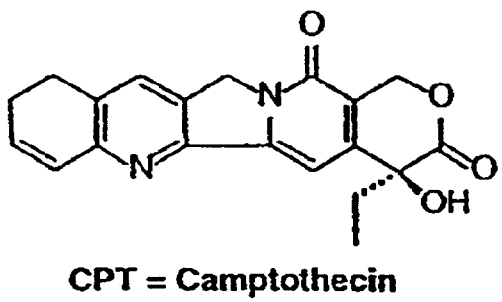
FIG. 11: shows the structure of reference compounds tested hereinbelow.
Figure 11:
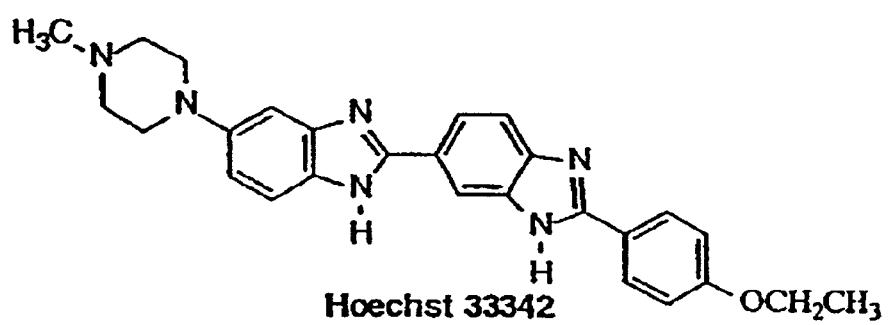
Figure 11:
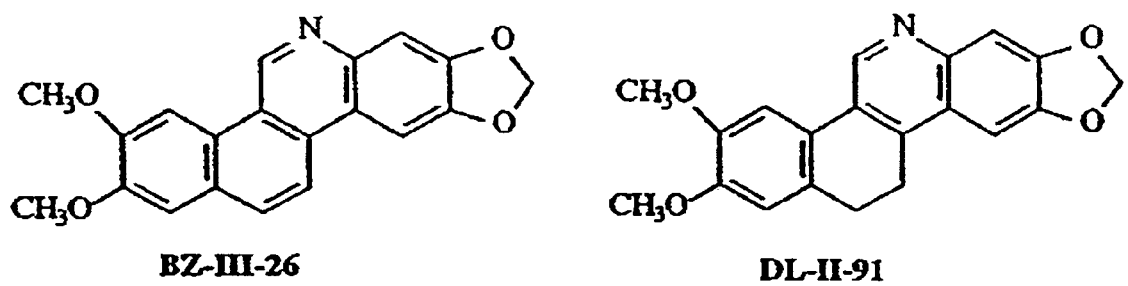

*See FIG. 11 [+]VBS = Vinblastine

The data in Tables 2 and 3 demonstrates that representative compounds of the invention function as cytotoxic agents against tumor cell lines, including multidrug resistant tumor cell lines. Thus, the compounds are useful to treat cancer and can be used to treat tumors that are resistant to other specific chemotherapeutic agents.

Topoisomerase inhibitors are also known to possess antibacterial, antifungal, antiprotozoal, antihelmetic, and antiviral activity. Accordingly, the topoisomerase inhibitors of the invention may also be useful as antibacterial, antifungal, antiprotozoal, antihelmetic, or antiviral agents. In particular, compounds of the invention that demonstrate little or no activity as mammalian topoisomerase I poisons, because of the possibility of similar molecular mechanism of action, could be highly active and selective antibacterial, antifungal, antiprotozoal, antihelmetic, or antiviral agents. Thus, certain compounds of the invention may be particularly useful as systemic antibacterial, antifungal, antiprotozoal, antihelmetic, or antiviral agents in mammals. The invention also provides the use of a compound of the invention for the manufacture of a medicament useful for producing an antibacterial, antifungal, antiprotozoal, antihelmetic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples, wherein unless otherwise stated:

TABLE 2

| [] $\mu M$ | KB3-1 (oral) | KBV-1 (mdr-1) | KBH1.0 + V (H033342r.) | HELA (cervical) | HCT116 (colon) | ZR-75-1 (breast) |
| --- | --- | --- | --- | --- | --- | --- |
| CPT* | 0.006 | 0.006 | 0.007 | 0.004 | 0.003 | 0.004 |
| VBS[+] | 0.003 | 0.4 | 0.0022 | 0.002 | 0.003 | 0.003 |
| HO33342* | 0.25 | 3 | >10 | 0.6 | 0.22 | 0.06 |
| BZ-III-26* | 0.3 | 0.2 | 0.15 | 0.15 | 0.25 | 0.2 |
| DL-II-91* | 0.2 | 0.18 | 0.12 | 0.12 | 0.2 | 0.2 |
| 6 | 6 | 4 | 5 | 6 | 3.2 | 4 |
| 14 | 0.07 | 0.08 | 0.06 | 0.05 | 0.035 | 0.04 | melting points were determined with a Thomas-Hoover Unimelt capillary melting point apparatus; column chromatography refers to flash chromatography conducted on Sil-iTech 32–63 m, (ICN Biomedicals, Eschwegge, Ger.) using the solvent systems indicated; radial chromatography refers to the use of a Model 8924 chromatotron (Harrison Research, Calif.); infrared spectral data (IR) were obtained on a Perkin-Elmer 1600 Fourier transform spectrophotometer and are reported in $cm^{-1}$; proton ($^1$H NMR) and carbon ($^{13}$C NMR) nuclear magnetic resonance were recorded on a Varian Gemini-200 Fourier Transform spectrometer; NMR spectra (200 MHz $^1$H and 50 MHz $^{13}$C) were recorded in the deuterated solvent indicated with chemical shifts reported in units downfield from tetramethylsilane (TMS); coupling constants are reported in hertz (Hz), a few drops of $CF_3COOH$ improved $^{13}$C NMR spectra by allowing for increased solubility and formation of the protonated form of the terbenzimidazoles, thereby eliminating tautomeric differences among carbon atoms; mass spectra were obtained from Washington University Resource for Biomedical and Bio-organic Mass Spectrometry within the Department of Chemistry at Washington University, St. Louis, Mo.; combustion analyses were performed by Atlantic Microlabs, Inc., Norcross, Ga., and were within 0.4% of the theoretical value; compounds 7 and 15 were prepared by nitration of 4-bromoveratrole and 4-bromo-1,2-(methylenedioxy) benzene as previously described (Pettit, G. R.; Piatak, D. M. *J. Org. Chem.*, 25, 1960, 721; Dallacker, F.; Wagner, A. Z. *Naturforsch.*, 1984, 39b, 936).

EXAMPLE 1

2,3-Dimethoxy-dibenzo[c,h]cinnoline (6).

6-(2-Aminophenyl)-2,3-dimethoxynaphthalene (5, 70 mg, 0.25 mmol) was dissolved in 48% hydrobromic acid (4.25 mL), cooled in ice-salt bath, and treated dropwise with stirring with sodium nitrite (0.13 g) in water (2.2 mL). Stirring was continued for 0.5 h., and to the cold solution was then added with stirring freshly precipitated copper (0.5 g). The mixture was allowed to rise slowly to room temperature and left overnight. The solid was filtered off and washed with hot chloroform. The chloroform solution was washed with diluted sodium hydroxide solution, then with water, dried (anhydrous $Na_2SO_4$) and rotaevaporated to give the crude product. Chromatography on silica gel using 50:50 hexanes:ethyl acetate afforded the title compound (13 mg) in 18% yield; $^1$H NMR ($CDCl_3$) d 4.11(3H, s), 4.24(3H, s), 7.37(1H, s), 7.89~7.94 (2H, m), 8.14(1H, d, J=8.9), 8.41(1H, d, J=8.8), 8.61~8.66(1H, m), 8.75~8.80(1H, m), 9.24(1H, s); $^{13}$C NMR d 56.1, 56.4, 104.0, 107.3, 112.3, 116.5, 118.5, 121.7, 126.7, 128.6, 128.8, 131.1, 131.2, 131.9, 141.5, 146.3, 150.9, 151.0.

The intermediate 6-(2-aminophenyl)-2,3-dimethoxynaphthalene (5) was prepared as follows.

a. 6-(2-Nitrophenyl)-2,3-dimethoxy-7,8-dihydronaphthalene (3)

$Pd(PPh_3)_2Cl_2$ (840 mg, 1.2 mmol) and sodium acetate (200 mg, 2.4 mmol) were added to a solution of 6,7-dimethoxy-3,4-dihydronaphthalene (2, 700 mg, 3.7 mmol) and 1-iodo-2-nitrobenzene (925 mg, 3.7 mmol) in dimethylacetamide (50 mL). The mixture was stirred under nitrogen at 140° C. overnight, and then concentrated in vacuo. Ethyl acetate (60 mL) was added to the residue and washed with distilled water (50 mL). The organic layer was separated and passed through a celite bed. The organic layer was then washed with brine, dried (anhydrous $Na_2SO_4$) and concentrated in vacuo. The residue was chromatographed to give compound 3 (330 mg) in 29% yield; $^1$H NMR ($CDCl_3$) d 2.51(2H, t, J=8.1), 2.92(2H, t, J=8.1), 3.87(3H, s), 3.90(3H, s), 6.45(1H, s), 6.67(1H, s), 6.73(1H, s), 7.38~7.45 (2H, m), 7.54~7.62(1H, m), 7.88~7.93(1H, m); $^{13}$C NMR d 28.5, 28.5, 56.6, 111.0, 111.7, 124.9, 127.0, 127.1, 128.1, 128:3, 131.3, 133.3, 135.7, 138.7, 147.9, 148.9.

b. 6-(2-Nitrophenyl)-2,3-dimethoxynaphthalene (4) 6-(2-Nitrophenyl)-2,3-dimethoxy-7,8-dihydronaphthalene (100 mg, 0.32 mmol) was refluxed overnight in toluene (20 mL) with DDQ (109 mg, 0.48 mmol). Cooled down to room temperature and filtered through celite bed. The filtrate was rotaevaporated to dryness to give the crude product. Chromatography on silica gel using 80:20 hexanes:ethyl acetate afforded compound 4 (90 mg) in 91% yield; $^1$H NMR ($CDCl_3$) d 4.00(3H, s), 4.01(3H, s), 7.12(1H, s), 7.14(1H, s), 7.27(1H, dd, J=8.4, J=1.7), 7.46~7.62(3H, m), 7.66(1H, s), 7.72(1H, d, J=8.4), 7.86(1H, d, J=8.1); $^{13}$C NMR d 56.4, 106.6, 107.1, 124.5, 124.6, 125.9, 127.3, 128.4, 129.3, 129.6, 132.7, 132.7, 133.6, 137.0, 149.9, 150.5, 150.6.

c. 6-(2-Aminophenyl)-2,3-dimethoxynaphthalene (5)

6-(2-Nitrophenyl)-2,3-dimethoxynaphthalene (70 mg, 0.23 mmol) was hydrogenated overnight in ethyl acetate (45 mL) at 40–45 lb./sq. in. under catalysis of palladium (10 wt % on activated carbon, 20 mg). The solution was passeded through a celite bed and the catalyst was washed with ethyl acetate (3×10 mL). Concentration in vacuo gave compound 5 (60 mg) in 99% yield; 1H NMR ($CDCl_3$) d 4.02(3H, s), 4.04(3H, s), 6.82(1H, d, J=8.0), 6.85~6.93 (1H, m), 7.16(1H, s), 7.18(1H, s), 7.20~7.26(2H m), 7.47(1H, dd, J=8.3, J=1.6), 7.78(1H, d, J=8.8), 7.80(1H, s); $^{13}$C NMR d 56.4, 106.6, 106.9, 116.1, 119.2, 126.1, 126.8, 127.3, 128.3, 128.7, 128.9, 129.9, 131.2, 135.8, 144.3, 150.2, 150.3.

Compound 2 was prepared as illustrated in FIG. 1, from readily available starting materials, using standard procedures.

EXAMPLE 2

2,3-Dimethoxy-8,9-methylenedioxy-dibenzo[c,h]cinnoline (14)

6-(2-Amino-4,5-methylenedioxyphenyl)-2,3-dimethoxynaphthalene (13, 40 mg, 0.13 mmol) in acetic acid (2 mL) and concentrated hydrochloric acid (0.3 mL) was cooled to 0° C. and diazotised with a solution of sodium nitrite (0.09 g in 1.5 mL water). The diazonium solution was allowed to rise slowly to room temperature and left overnight. Water (50 mL) was added to the red solution with some precipitate. The resulting mixture was extracted with ethyl acetate, washed with diluted sodium hydroxide solution, then with water, dried (anhydrous $Na_2SO_4$) and rotaevaporated to give the crude product. Chromatography on silica gel using 40:60 hexanes:ethyl acetate afforded the title compound (20 mg) in 50% yield; $^1$H NMR ($CDCl_3$) d 4.09(3H, s), 4.22(3H, s), 6.24(2H, s), 7.31(1H, s), 7.80(1H s), 7.95(1H, s), 8.00(1H, d, J=9.2), 8.13(1H, d, J=8.9), 9.14(1H, s); $^{13}$C NMR d 56.5 56.9, 98.1, 102.9, 104.6, 107.5, 107.9, 117.1, 119.6, 120.6, 126.8, 128.5, 131.7, 141.9, 145.6, 150.2, 151.2, 152.1.

The intermediate 6-(2-Amino-4,5-methylenedioxyphenyl)-2,3-dimethoxynaphthalene (13) was prepared as follows.

a. 6,7-Dimethoxy-3,4-dihydro-2-naphthalenetriflate (9)

A solution of 6,7-dimethoxy-2-tetralone (250 mg, 1.2 mmol) in THF (5 mL) was added to a suspension of sodium hydride (60 wt %, 75 mg, 1.9 mmol) in THF (10 mL) cooled by ice bath and stirred 0.5 h. A solution of N-phenyltrifluoromethane-sulfonimide (500 mg, 1.4 mmol) in THF (5 mL) was then added, and the reaction was stirred at 0° C. for 9 hours. After concentration in vacuo, the residue was chromatographed using 80:20 hexanes:ethyl acetate to give compound 9 (300 mg) in 73% yield; $^1$H NMR ($CDCl_3$) d 2.66(2H, t, J=8.5), 3.00(2H, t, J=8.4), 3.86(3H, s), 3.88

(3H, s), 6.40(1H, s), 6.62(1H, s), 6.68(1H, s); $^{13}$C NMR d 27.1, 28.9, 56.5, 111.3, 111.7, 115.9, 118.7, 122.3, 124.0, 126.0, 148.2, 148.9, 149.3.

b. 6,7-Dimethoxy-2-naphthalenetriflate (10)

6,7-Dimethoxy-3,4-dihydro-2-naphthalenetriflate (200 mg, 0.59 mmol) was refluxed overnight in toluene (30 mL) with DDQ (166 mg, 0.73 mmol), cooled to room temperature, and filtered through celite bed. The filtrate was concentrated in vacuo to give the crude product. Chromatography on silica gel using a 80:20 hexanes:ethyl acetate afforded compound 10 (190 mg) in 95% yield; $^1$H NMR (CDCl$_3$) d 4.00(6H, s), 7.10(1H, s), 7.12(1H, s), 7.21(1H, dd, J=8.9, J=2.5), 7.58(1H, d, J=2.5), 7.71(1H, d, J=8.9); $^{13}$C NMR d 56.4, 106.6, 106.6, 109.7, 116.1, 117.9, 118.2, 122.5, 128.9, 129.0, 129.8, 146.6, 150.9, 151.3.

c. 6-(4,5-Methylenedioxy-2-nitrophenyl)-2,3-dimethoxynaphthalene (12)

Tetrakis(triphenylphosphine)palladium(0) (40 mg) and cuprous bromide (8 mg) were added to a solution of 6,7-dimethoxy-2-naphthalenetriflate (160 mg, 0.48 mmol) and trimethyl(3,4-methylenedioxy-6-nitrophenyl)stannane (8, 187 mg, 0.57 mmol) in THF (20 mL). The mixture was stirred at room temperature for 0.5 h., and then refluxed under nitrogen for 18 h. After Cooling, THF was rotaevaporated and ethyl acetate (50 ml) was added to the residue. the solution was washed with water (30 mL). The organic layer was separated and passed through a celite bed to remove suspended particles. The organic layer was then washed with brine, dried (anhydrous Na$_2$SO$_4$) and concentrated in vacuo. The residue was chromatographed on silica gel using 70:30 hexanes:ethyl acetate to give a mixture of two compounds with same R$_f$ value. The mixture can be separated after the hydrogenation step.

d. 6-(2-Amino-4,5-methylenedioxyphenyl)-2,3-dimethoxynaphthalene (13)

6-(4,5-Methylenedioxy-2-nitrophenyl)-2,3-dimethoxynaphthalene (25 mg, 0.071 mmol) was hydrogenated overnight in ethyl acetate (40 mL) at 40~45 lb./sq. in. under catalysis of palladium (10 wt % on activated carbon, 20 mg). The solution was passed through celite bed and the catalyst was washed with ethyl acetate (3×10 ml). Concentration in vacuo gave the crude product. Chromatography using 60:40 hexanes:ethyl acetate gave compound 13 (15 mg) in 66% yield; $^1$H NMR (CDCl$_3$) d 4.01(3H, s), 4.02(3H, s), 5.91(2H, s), 6.40(1H, s), 6.73(1H, s), 7.13(1H, s), 7.15 (1H, s), 7.39(1H, dd, J=8.2, J=1.8), 7.72(1H, s), 7.74(1H, d, J=8.5); $^{13}$C NMR d 56.4, 98.3, 101.2, 106.6, 106.8, 110.7, 120.5, 126.3, 127.0, 127.3, 128.5, 129.9, 135.7, 138.9, 141.1, 148.0, 150.1, 150.3.

The intermediate trimethyl(3,4-methylenedioxy-6-nitrophenyl)-stannane (8) in sub-part c above was prepared as follows.

e. Trimethyl (3,4- methylenedioxy-6-nitrophenyl)stannane (8)

A mixture of hexmethylditin (3 g, 9.2 mmol), 4-bromoveratrole 7 (Pettit, G. R.; Piatak, D. M. *J. Org. Chem.*, 25, 1960, 1.6 g, 6.1 mmol) and Pd(PPh$_3$)$_4$ (200 mg) in anhydrous THF (30 ml) was heated to reflux under nitrogen for 10 h. After cooling to room temperature, THF was evaporated and methylene chloride (30 mL) was added to the residue. To this mixture, aqueous potassium fluoride (7.0M, 2 mL) was added dropwise with vigorous stirring. The mixture was passed through a celite bed and the filtrate was washed with brine. The methylene chloride layer was dried (anhyd. Na$_2$SO$_4$), filtered and evaporated in vacuo. The residue was chromatographed over 100 g of silica gel using 1:6 ethyl acetate:hexanes to give 8 in 65% yield; $^1$H NMR (CDCl$_3$) d 0.32 (9H, s), 6.12 (2H, s), 7.04 (1H, s), 7.82 (1H, s); $^{13}$C NMR (CDCl$_3$) d −6.8, 103.3, 105.8, 114.5, 137.2, 147.9, 149.4, 153.4; HRMS calcd for C$_{10}$H$_{13}$NO$_4$Sn—CH$_3$: 315.9632; found: 315.9638.

EXAMPLE 3

2,3,8,9-Tetramethoxy-dibenzo[c,h]cinnoline (19)

6-(2-Amino-4,5-dimethoxyphenyl)-2,3-dimethoxynaphthalene (18) (11 mg, 0.033 mmol) in acetic acid (0.6 mL) and concentrated hydrochloric acid (0.06 mL) was cooled to 0° C. and diazotised with a solution of sodium nitrite (0.026 g in 0.5 mL water). The diazonium solution was allowed to rise slowly to room temperature and left overnight. Water (30 mL) was added to the red solution with some precipitate. The resulting mixture was extracted with ethyl acetate, washed with diluted sodium hydroxide solution, then with water, dried (anhydrous Na$_2$SO$_4$) and rotaevaporated to give the crude product. Chromatography on silica gel using 40:60 chloroform:ethyl acetate afforded the title compound (5 mg) in 44% yield; $^1$H NMR (CDCl$_3$) d 4.09(3H, s), 4.18(6H, s), 4.23(3H, s), 7.31(1H, s), 7.74(1H, s), 8.00(1H, s), 8.01(1H, d, J=8.5), 8.20(1H, d, J=8.9), 9.15(1H, s); $^{13}$C NMR d 56.5, 56.9, 99.9, 104.5, 107.9, 109.5, 116.9, 118.5, 118.9, 127.0, 128.4, 131.6, 141.8, 144.6, 151.1, 151.2, 152.0, 153.9.

The intermediate 6-(2-amino-4,5-dimethoxyphenyl)-2,3-dimethoxynaphthalene (18) was prepared as follows.

a. Trimethyl(3,4-dimethoxy-6-nitrophenyl)stannane (16)

A mixture of hexmethylditin (3 g, 9.2 mmol), 4-bromo-1,2-(methylenedioxy)benzene 15 (Dallacker, F.; Wagner, A. Z. *Naturforsch.*, 1984, 39b, 93b, 1.6 g, 6.1 mmol) and Pd(PPh$_3$)$_4$ (200 mg) in anhydrous THF (30 ml) was heated to reflux under nitrogen for 10 h. After cooling to room temperature, THF was evaporated and methylene chloride (30 mL) was added to the residue. To this mixture, aqueous potassium fluoride (7.0M, 2 mL) was added dropwise with vigorous stirring. The mixture was passed through a celite bed and the filtrate was washed with brine. The methylene chloride layer was dried (anhyd. Na$_2$SO$_4$), filtered and evaporated in vacuo. The residue was chromatographed over 100 g of silica gel using 1:6 ethyl acetate:hexanes to give 16 in 70% yield; mp 115–117° C.; $^1$H NMR (CDCl$_3$) d 0.32 (9H, s), 3.94 (3H, s), 3.99 (3H, s), 7.03 (1H, s), 7.88 (1H, s); $^{13}$C NMR (CDCl$_3$) d −7.2, 56.7, 107.7, 117.3, 134.0, 146.8, 149.8, 154.1; HRMS calcd for C$_{11}$H$_{17}$NO$_4$Sn—CH$_3$: 329.9937; found: 329.9939.

b. 6-(4,5-Dimethoxy-2-nitrophenyl)-2,3-dimethoxynaphthalene (17)

Tetrakis(triphenylphosphine)palladium(0) (80 mg) and cuprous bromide (16 mg) were added to a solution of 6,7-dimethoxy-2-naphthalenetriflate (10, 220 mg, 0.655 mmol) and trimethyl(3,4-dimethoxy-6-nitrophenyl)stannane (16, 220 mg, 0.64 mmol) in THF (25 mL). The mixture was stirred at room temperature for 0.5 h., and then refluxed under nitrogen for 32 hr. After Cooling, THF was rotaevaporated and ethyl acetate (50 ml) was added to the residue the solution was washed with water (30 mL). The organic layer was separated and passed through a celite bed to remove suspended particles. The organic layer was then washed with brine, dried (anhydrous Na$_2$SO$_4$) and concentrated in vacuo. The residue was chromatographed on silica gel using 60:40 hexanes:ethyl acetate to give compound 17; $^1$H NMR (CDCl$_3$) d 3.95(3H, s), 3.99(6H, s), 4.01(3H, s), 6.86(1H, s), 7.12(1H, s), 7.14(1H, s), 7.23(1H, dd, J=8.4, J=1.8), 7.56(1H, s), 7.61(1H, d, J=1.7), 7.70(1H, d, J=8.4); $^{13}$C NMR d 56.4, 56.9, 106.7, 107.0, 108.3, 114.4, 124.9, 125.7, 127.0, 129.0, 129.5, 132.2, 134.6, 141.6, 148.4, 150.4, 152.7.

c. 6-(2-Amino-4,5-dimethoxyphenyl)-2,3-dimethoxynaphthalene (18)

6-(4,5-Dimethoxy-2-nitrophenyl)-2,3-dimethoxynaphthalene (12 mg, 0.03 mmol) was hydrogenated overnight in ethyl acetate (20 mL) at 40–45 lb./sq. in. under catalysis of palladium (10 wt % on activated carbon, 10 mg). The solution was passed through celite bed and the catalyst was washed with ethyl acetate (3×10 mL). Concentration in vacuo gave the crude product. Chromatography using 65:35 hexanes:ethyl acetate gave compound 18 (11 mg) in nearly 100% yield; $^1$H NMR (CDCl$_3$) d 3.84(3H, s), 3.89(3H, s), 4.01(3H, s), 4.02(3H, s), 6.41(1H, s), 6.80(1H, s), 7.14(1H, s), 7.15(1H, s), 7.43(1H, dd, J=8.4, J=1.6), 7.75(1H, d, J=1.5), 7.75(1H, d, J=8.4); $^{13}$C NMR d 56.4, 57.2, 101.3, 106.6, 106.8, 115.2, 119.9, 126.2, 126.8, 127.3, 128.5, 129.9, 135.7, 138.0, 142.7, 149.8, 150.1, 150.3.

EXAMPLE 4

2,3,8-Trimethoxydibenzo[c,h]cinnoline (60)

6-(2-Amino-4-methoxyphenyl)-2,3-dimethoxynaphthalene (32) (12 mg, 0.039 mmol) was dissolved in acetic acid (0.6 mL) and concentrated hydrochloric acid (0.06 mL). The solution was cooled in an ice bath and diazotized by the dropwise addition of a solution of sodium nitrite (0.026 g in 0.5 mL water). The resulting diazonium solution was allowed to rise to room temperature slowly and left overnight. To the resulting red solution which contained some precipitate was added 30 mL water and the mixture was extracted with ethyl acetate (30 mL×3). The organic layers were combined and washed with diluted sodium hydroxide solution first, then with water and brine. The ethyl acetate extracts were dried with anhydrous sodium sulfate and evaporated in vacuo. The crude product was purified by column chromatography on silica gel using 40:60 hexanes:ethyl acetate to give the pure 4 (5 mg) in 40% yield; mp 244–246° C.; IR (KBr) 2919, 1619, 1507, 1388, 1292, 1277, 1204 cm$^{-1}$; UV (MeOH) 292, 266, 216 nm; $^1$H NMR (CDCl$_3$) δ4.10 (6H, s), 4.22 (3H, s), 7.32 (1H, s), 7.54 (1H, dd, J$_1$=9.1, J$_2$=2.6), 8.04–8.08 (2H, m), 8.28 (1H, d, J=8.9), 8.49 (1H, d, J=9.1), 9.16 (1H, s); $^{13}$C NMR δ56.33, 56.52, 56.92, 104.36, 107.93, 108.92, 116.88, 117.08, 119.48, 123.51, 124.54, 127.14, 128.42, 132.46, 141.77, 148.52, 151.12, 151.40, 160.45; HRMS (EI) calcd for C$_{19}$H$_{16}$N$_2$O$_3$ m/z: 320.1161; found: 320.0384.

The intermediate compound 32 was prepared as follows.

a. 6-(4-Methoxy-2-nitrophenyl)-2,3-dimethoxynaphthalene (29)

Tetrakis(triphenylphosphine)palladium (0) (60 mg) and cuprous bromide (10 mg) were added to a solution of 6,7-dimethoxy-2-trifluoromethanesulfonyloxy-naphthalene 10 (150 mg, 0.45 mmol) and trimethylnitroarylstannane 26 (140 mg, 0.45 mmol) in THF (20 mL) at room temperature and stirred for 0.5 h. The mixture was then refluxed under N$_2$ for 36 h. After cooling, THF was evaporated and ethyl acetate (30 mL) was added to the residue. The solution was washed with water. The organic layer was separated and passed through a Celite bed to remove suspended particles. The organic layer was then washed with brine, dried (anhydrous Na$_2$SO$_4$), and evaporated in vacuo. The residue was chromatographed using a 70:30 mixture of hexanes:ethyl acetate to give 29 (60 mg) in 43% yield; $^1$H NMR (CDCl$_3$) δ3.92 (3H, s), 4.01 (3H, s), 4.02 (3H, s), 7.12–7.26 (4H, m), 7.39–7.46 (2H, m), 7.61 (1H, d, J=1.7), 7.71 (1H, d, J=8.4); $^{13}$C NMR (CDCl$_3$) δ56.42, 106.64, 106.98, 109.50, 119.23, 124.83, 125.89, 127.20, 129.02, 129.38, 129.60, 133.53, 150.25, 150.42, 159.46; HRMS (EI) calcd for C$_{19}$H$_{17}$NO$_5$ m/z: 339.1107; found: 339.1108.

b. 6-(2-Amino-4-methoxyphenyl)-2,3-dimethoxynaphthalene (32)

6-(4-Methoxy-2-nitrophenyl)-2,3-dimethoxynaphthalene 29 (18 mg, 0.053 mmol) was hydrogenated overnight in ethyl acetate (20 mL) at 40–45 lb./sq. in. using 10% palladium on carbon (10 mg) as catalyst. The reaction solution was passed through a Celite bed and the catalyst was washed with ethyl acetate (10 mL×3). Concentration in vacuo gave the crude product. The residue was chromatographed using a 60:40 mixture of hexanes:ethyl acetate to give 32 (14 mg) in 85% yield; $^1$H NMR (CDCl$_3$) δ3.83 (3H, s), 4.01 (3H, s), 4.03 (3H, s), 6.37 (1H, d, J=2.5), 6.45 (1H, dd, J$_1$=8.3, J$_2$=2.4), 7.12–7.16 (3H, m), 7.42 (1H, dd, J$_1$=8.4, J$_2$=1.7), 7.72–7.77 (2H, m); $^{13}$C NMR δ55.72, 56.40, 101.56, 104.79, 106.59, 106.78, 121.49, 126.36, 126.81, 127.24, 128.47, 129.89, 131.98, 135.55, 145.28, 150.01, 150.25, 160.49; HRMS (EI) calcd for C$_{19}$H$_{19}$NO$_3$ m/z: 309.1365; found: 309.1355.

The intermediate compound 26 used in sub-part a above was prepared as follows.

c. Trimethyl(4-methoxy-2-nitrophenyl)stannane (26)

A mixture of hexamethylditin (1.0 g, 3.1 mmol), 4-methoxy-2-nitrobromobenzene 23 (0.5 g, 2.16 mmol) and Pd(PPh$_3$)$_4$ (60 mg) in anhydrous THF (20 mL) was heated to reflux under nitrogen until thin layer chromatography no longer showed the presence of starting material. After cooling to room temperature, THF was evaporated and methylene chloride was added to the residue. To this mixture, aqueous potassium fluoride (7.0 M, 1.0 mL) was added dropwise with vigorous stirring. The mixture was passed through a Celite bed and the filtrate washed with brine. The methylene chloride layer was dried (anhydrous Na$_2$SO$_4$), filtered and the solution concentrated in vacuo. The residue was chromatographed using a 95:5 mixture of hexanes:ethyl acetate to give 26 (260 mg) in 38% yield; mp 93–5° C.; $^1$H NMR (CDCl$_3$) δ0.32 (9H, s), 3.89 (3H, s), 7.21 (1H, dd, J$_1$=8.0, J$_2$=2.6), 7.57 (1H, d, J=8.0), 7.86 (1H, d, J=2.6); $^{13}$C NMR (CDCl$_3$) δ−7.1, 56.7, 107.7, 117.3, 133.9, 146.8, 149.6, 154.1; HRMS (EI) calcd for C$_{10}$H$_{15}$NO$_3$Sn—CH$_3$ m/z: 301.9839; found: 301.9832.

The starting 4-Bromo-3-nitroanisole (23) was purchased from Aldrich Chemical Company (Milwaukee, Wis.) [5344-78-5].

EXAMPLE 5

2,3,9-Trimethoxydibenzo[c,h]cinnoline (61)

6-(2-Amino-5-methoxyphenyl)-2,3-dimethoxynaphthalene (33) (60 mg, 0.20 mmol) was dissolved in acetic acid (1.5 mL) and concentrated hydrochloric acid (0.3 mL). The solution was cooled in an ice bath and diazotized by dropwise addition of a solution of sodium nitrite (0.12 g in 1.2 mL water). The resulting diazonium solution was allowed to rise to room temperature slowly and left overnight. To the resulting red solution with some precipitate, 50 mL water was added and then extracted with ethyl acetate (40 mL×3). The organic layers were combined and washed with diluted sodium hydroxide solution first, then with water and brine. Dried with anhydrous sodium sulfate and evaporated in vacuo. The crude product was purified by column chromatography on silica gel using 35:65 hexanes:ethyl acetate to give the pure 5 (16 mg) in 26% yield; mp 215–217° C.; IR (KBr) 2987, 1617, 1504, 1486, 1394, 1277, 1231, 1167 cm$^{-1}$; UV (MeOH) 288, 262, 232 nm (log ε=4.71, 4.66, 4.58); $^1$H NMR (CDCl$_3$) δ4.07 (3H, s), 4.09 (3H, s), 4.22 (1H, s), 7.29 (1H, s), 7.46 (1H, dd, J$_1$=9.1, J$_2$=2.6), 7.72 (1H, J=2.5), 7.99 (1H, d, J=8.9), 8.20 (1H, d, J=9.0), 8.60 (1H, d, J=9.1), 9.17 (1H, s); $^{13}$C NMR δ56.31, 56.51, 56.90, 100.27, 104.61, 107.73, 117.00, 118.66, 121.31, 124.25, 126.98, 129.09, 131.40, 133.34, 141.76, 143.70, 151.23, 151.31, 161.95; HRMS (EI) calcd for $C_{19}H_{16}N_2O_3$ m/z: 320.1161; found: 320.1144.

The intermediate compound 33 was prepared as follows.

a. 6-(5-Methoxy-2-nitrophenyl)-2,3-dimethoxynaphthalene (30)

Tetrakis(triphenylphosphine)palladium (0) (80 mg) and cuprous bromide (6 mg) were added to a solution of 6,7-dimethoxy-2-trifluoromethanesulfonyloxy-naphthalene 10 (200 mg, 0.60 mmol) and trimethylnitroarylstannane 27 (200 mg, 0.64 mmol) in THF (25 mL) at room temperature and stirred for 0.5 h. The mixture was then refluxed under $N_2$ overnight. After cooling, THF was evaporated and ethyl acetate (30 mL) was added to the residue. The solution was washed with water. The organic layer was separated and passed through a Celite bed to remove suspended particles. The organic layer was then washed with brine, dried (anhydrous $Na_2SO_4$), and evaporated in vacuo. The residue was chromatographed using a 75:25 mixture of hexanes:ethyl acetate to give a mixture of two compounds with similar $R_f$ values. This mixture was used for next step without further purification.

b. 6-(2-Amino-5-methoxyphenyl)-2,3-dimethoxynaphthalene (33)

Crude 6-(5-methoxy-2-nitrophenyl)-2,3-dimethoxynaphthalene 30 (100 mg, approximately 90% pure) was hydrogenated overnight in ethyl acetate (40 mL) at 40–45 lb./sq. in. using 10% palladium on carbon (30 mg) as catalyst. The reaction solution was passed through a Celite bed and the catalyst was washed with ethyl acetate (10 mL×3). Concentration in vacuo gave the crude product. The residue was chromatographed using a 50:50 mixture of hexanes:ethyl acetate to give 33 (66 mg); mp 158–160° C.; IR (KBr) 3408, 3354, 2936, 1633, 1499, 1249, 1166 cm$^{-1}$; $^1$H NMR (CDCl$_3$) δ3.57 (2H, s), 3.79 (3H, s), 4.01 (3H, s), 4.03 (3H, s), 6.77–6.84 (3H, m), 7.15 (1H, s), 7.16 (1H, s), 7.45 (1H, dd, $J_1$=8.3, $J_2$=1.8), 7.75–7.79 (2H, m); $^{13}$C NMR δ56.34, 56.42, 106.59, 106.85, 114.80, 116.35, 117.41, 125.99, 126.81, 127.32, 128.73, 129.42, 129.82, 135.75, 137.89, 150.19, 150.32, 153.25; HRMS (EI) calcd for $C_{19}H_{19}NO_3$ m/z: 309.1365; found: 309.1375.

The intermediate compound 27 was perpared as follows.

c. 3-Methoxy-6-nitrobromobenzene (24)

Nitric acid (70%, 5 mL) was placed in a 25 mL round-bottomed flask. Concentrated sulphuric acid (4 mL) was then added dropwise with stirring. The mixture was kept cool during the addition by immersing the flask in an ice bath. 3-Methoxybromobenzene (4 g, 21.5 mmol) was then introduced dropwise. The reaction mixture was then heated to 50° C. and stirred for 5 h. After cooling, the mixture was poured into 100 mL of cold water and extracted with ethyl acetate (30 mL×3). The organic layers were combined and washed with water (50 mL×4) and brine. The ethyl acetate layer was dried with anhydrous sodium sulfate and concentrated in vacuo. The crude product was purified by column chromatography on silica gel using 95:5 hexanes:ethyl acetate. The first compound that eluted from the column was 3-methoxy-6-nitrobromobenzene (1.2 g) in 24% yield; 1H NMR (CDCl$_3$) δ3.96(3H, s), 7.17 (1H, dd, $J_1$=8.6, $J_2$=1.9), 7.24 (1H, d, J=1.9), 7.75 (1H, d, J=8.6); $^{13}$C NMR δ57.34 117.58, 124.00, 127.41, 129.05, 142.26, 154.02. The second compound eluting from the column was 24 (1.5 g, 30% yield); 43–45° C.; $^1$H NMR (CDCl$_3$) δ3.89 (3H, s), 6.91 (1H, dd, $J_1$=9.1, $J_2$=2.7), 7.21 (1H, d, J=2.7), 7.98 (1H, d, J=9.1); $^{13}$C NMR δ56.68, 114.02, 117.29, 120.61, 128.46, 163.23.

d. Trimethyl(3-methoxy-6-nitrophenyl)stannane (27)

A mixture of hexamethylditin (2 g, 6.13 mmol), 3-methoxy-6-nitrobromobenzene 24 (0.70 g, 3.0 mmol) and Pd(PPh$_3$)$_4$ (100 mg) in anhydrous THF (20 mL) was heated to reflux under nitrogen until thin layer chromatography no longer showed the presence of starting material. After cooling to room temperature, THF was evaporated and methylene chloride was added to the residue. To this mixture, aqueous potassium fluoride (7.0 M, 1.5 mL) was added dropwise with vigorous stirring. The mixture was passed through a Celite bed and the filtrate washed with brine. The methylene chloride layer was dried (anhydrous $Na_2SO_4$), filtered and the solution concentrated in vacuo. The residue was chromatographed using a 500:8 mixture of hexanes:ethyl acetate to give 27 (200 mg) in 21% yield; 1H NMR (CDCl$_3$) δ0.34 (9H, s), 3.91 (3H, s), 6.92 (1H, dd, $J_1$=9.1, $J_2$=2.7), 7.13 (1H, d, J=2.8), 8.33 (1H, d, J=9.1); $^{13}$C NMR δ–7.09, 56.23, 114.22, 122.38, 127.03, 143.62, 146.84, 164.05.

EXAMPLE 6

9-Hydroxy-2,3,8-trimethoxydibenzo[c,h]cinnoline (34)

9-Benzyloxy-2,3,8-trimethoxydibenzo[c,h]cinnoline, 42, (5 mg, 0.012 mmol) was hydrogenated overnight in ethyl acetate (25 mL) at 26 lb./sq. in. using 10% palladium on carbon (1.5 mg). The solution was passed through a Celite bed and the catalyst was washed with ethyl acetate (10 mL×3). Concentration of the ethyl acetate solution in vacuo gave the crude product. Chromatography using a 50:45:5 mixture of hexanes:ethyl acetate:methanol as eluting solvent gave compound 34 (3 mg) in 76% yield; 1H NMR (DMSO-d$_6$) δ4.00 (3H, s), 4.10 (3H, s), 4.12 (3H, s), 7.66 (1H, s), 8.02 (2H, s), 8.21 (1H, d, J=8.4), 8.38 (1H, d, J=8.9), 8.96 (1H, s); $^{13}$C NMR δ55.9, 56.4, 103.1, 103.8, 108.5, 109.1, 117.4, 117.8, 118.0, 125.7, 128.1, 131.3, 140.4, 143.8, 150.5, 150.7, 151.3, 152.4; HRMS (EI) calcd for $C_{19}H_{16}N_2O_4$ m/z 336.111; found: 336.1109.

EXAMPLE 7

9-Benzyloxy-2,3,8-trimethoxydibenzo[c,h]cinnoline (42)

6-(2-Amino-5-benzyloxy-4-methoxyphenyl)-2,3-dimethoxy-naphthalene 41 (35 mg, 0.084 mmol) was dissolved in acetic acid (0.65 mL) and concentrated hydrochloric acid (0.13 mL). The solution was cooled in an ice bath and diazotized by the dropwise addition of a solution of sodium nitrite (0.052 g in 0.52 mL water). The reaction mixture was allowed to warm slowly to room temperature and left for 1 day. To the resulting red solution containing some precipitate was added 50 mL water and the mixture was extracted with ethyl acetate (30 mL×3). The organic layers were combined and washed with diluted sodium hydroxide solution first, then with water and brine. The organic layer was dried using anhydrous sodium sulfate and evaporated in vacuo. The crude product was purified by column chromatography on silica gel using 20:80 hexanes:ethyl acetate to give the pure 42 (24 mg) in 67% yield; mp 244–246° C.; IR (KBr) 2935, 1621, 1507, 1466, 1307, 1269, 1234, 1206, 1168 cm$^{-1}$; $^1$H NMR (CDCl$_3$) δ4.07 (3H, s), 4.14 (3H, s), 4.21 (3H, s), 5.40 (2H, s), 7.25 (1H, s), 7.37–7.60 (5H, m), 7.91 (1H, d, J=9.0), 7.97 (1H, s), 8.01 (1H, d, J=9.0), 9.11 (1H, s); $^{13}$C NMR δ56.48, 56.86, 56.91, 71.64, 101.69, 104.43, 107.82, 109.58, 116.84, 118.19, 118.81, 126.95, 127.97, 128.34, 128.90, 129.34, 131.51, 136.31, 141.61, 144.52, 151.00, 151.14, 152.31, 152.93; HRMS (EI) calcd for $C_{26}H_{22}N_2O_4$ m/z: 426.1580; found: 426.1577.

The intermediate compound 41 was prepared as follows.

a. 5-Bromo-2-methoxyphenol (35)

To a solution of 5-bromo-2-methoxybenzaldehyde (2.4 g, 11.2 mmol) in 50 mL $CH_2Cl_2$, m-chloroperbenzoic acid (70–75%, 7 g, 28.4 mmol pure m-CPBA,) was added and the mixture was stirred at ambient temperature for 2 days. The reaction was quenched with aqueous saturated $NaHCO_3$ solution and extracted with ethyl acetate (50 mL×3). The organic extract was dried with anhydrous sodium sulfate and filtered through a silica gel bed. Evaporation of the solvent gave compound 35 (2.1 g) in 92% yield; mp 62–64° C.; $^1$H NMR ($CDCl_3$) δ3.87 (3H, s), 6.71 (1H, d, J=8.6), 6.97 (1H, dd, $J_1$=8.6, $J_2$=2.4), 7.07 (1H, d, J=2.4); $^{13}$C NMR δ56.59, 112.36, 113.75, 118.33, 123.29, 146.37, 146.98.

b. 3-Benzyloxy-1-bromo-4-methoxybenzene (36)

A solution of 5-bromo-2-methoxyphenol, 35, (2.0 g, 10 mmol) and α-bromotoluene (2.6 g, 15.3 mmol) in $CH_3CN$ (30 mL) and acetone (25 mL) was treated with potassium carbonate (2.1 g, 15.2 mmol). The resulting mixture was heated to reflux under nitrogen for 18 h. After cooling to room temperature, the reaction mixture was filtered through a Celite bed. The acetone was removed in vacuo and 50 mL ethyl acetate was added to the residue. The ethyl acetate solution was washed with water, brine, dried with anhydrous $NA_2SO_4$, and then evaporated in vacuo. The residue was chromatographed using a 90:10 mixture of hexanes:ethyl acetate to give compound 36 (2.77 g) in 96% yield; mp 70–71° C.; $^1$H NMR ($CDCl_3$) δ3.86 (3H, s), 5.12 (2H. s), 7.77 (1H, J=9.2), 7.04–7.08 (2H, m), 7.33–7.48 (5H, m); $^{13}$C NMR δ56.66, 71.68, 113.04, 113.54, 117.71, 124.47, 127.91, 128.58, 129.13, 136.91, 149.45, 149.50; HRMS (EI) calcd for $C_{14}H_{13}O_2Br$ m/z: 292.0099; found: 292.0085.

c. 3-Benzyloxy-4-methoxy-6-nitrobromobenzene (37)

3-Benzyloxy-1-bromo-4-methoxybenzene, 36, (1 g, 3.4 mmol) was dissolved in 50 mL acetic acid in a 100 mL round-bottomed flask and cooled to 0° C. using an ice bath. 2.5 mL nitric acid (70%) in 6 mL acetic acid was added dropwise. The reaction mixture was allowed to slowly rise to room temperature. After 3 h no starting material was detected by thin layer chromatography. Evaporation of acetic acid gave the crude product, which was filtered through a short silica gel column using a 80:20 mixture of hexanes:ethyl acetate to give 3-benzyloxy-4-methoxy-6-nitrobromobenzene (1.15 g) in quantitative yield; mp 134–135° C.; IR (KBr) 2946, 1577, 1518, 1468, 1382, 1329, 1266, 1211 cm$^{-1}$; UV (MeOH) 246, 212 nm (log ε=3.91, 4.13); $^1$H NMR ($CDCl_3$) δ3.93 (3H, s), 5.19 (2H. s), 7.17 (1H, s), 7.38–7.45 (5H, m), 7.57 (1H, s); $^{13}$C NMR δ56.99, 71.98, 107.69, 109.74, 118.73, 127.98, 129.11, 129.36, 135.50, 142.42, 149.18, 152.44; HRMS (EI) calcd for $C_{14}H_{12}NO_4Br$ m/z: 336.9950; found: 336.9941.

d. Trimethyl(3-benzyloxy-4-methoxy-6-nitrophenyl) stannane (38)

A mixture of hexamethylditin (2 g, 6.13 mmol), 3-benzyloxy-4-methoxy-6-nitro-bromobenzene 37 (1.4 g, 4.14 mmol) and $Pd(PPh_3)_4$ (200 mg) in anhydrous THF (40 mL) was heated to reflux under nitrogen for 2 days. After cooling to room temperature, THF was evaporated and methylene chloride was added to the residue. To this mixture, aqueous potassium fluoride (7.0 M, 1.5 mL) was added dropwise with vigorous stirring. The mixture was passed through a Celite bed and the filtrate washed with brine. The methylene chloride layer was dried (anhydrous $Na_2SO_4$), filtered and evaporated in vacuo. The residue was chromatographed using a 90:10 mixture of hexanes:ethyl acetate to give 38 (1.16 g) in 66% yield; mp 81–83° C.; IR (KBr) 2908, 1569, 1518, 1454, 1318, 1275, 1215 cm$^{-1}$; UV (MeOH) 248, 214 nm (log ε=4.08, 4.21); $^1$H NMR ($CDCl_3$) δ0.27 (9H, s), 3.97 (3H, s), 5.29 (2H. s), 7.04 (1H, J=9.2), 7.36–7.44 (5H, m), 7.91 (1H, s); $^{13}$C NMR δ–7.17, 56.75, 71.59, 108.01, 119.5, 127.80, 128.85, 129.31, 123.64, 136.42, 146.89, 150.18, 153.25; HRMS (EI) calcd for $C_{17}H_{21}NO_4Sn$ m/z: 408.0258; found: 408.0243.

e. 6-(5-Benzyloxy-4-methoxy-2-nitrophenyl)-2,3-dimethoxy-naphthalene (39)

Tetrakis(triphenylphosphine)palladium (0) (200 mg) and cuprous bromide (20 mg) were added to a solution of 6,7-dimethoxy-2-trifluoromethanesulfonyloxy-naphthalene 10 (500 mg, 1.49 mmol) and trimethylnitroarylstannane 38 (950 mg, 2.25 mmol) in THF (40 mL) at room temperature and stirred for 0.5 h. The mixture was then refluxed under $N_2$ for 2 days. After cooling, THF was evaporated and ethyl acetate (30 mL) was added to the residue. The solution was washed with water. The organic layer was separated and passed through a Celite bed to remove suspended particles. The organic layer was then washed with brine, dried (anhydrous $Na_2SO_4$), and evaporated in vacuo. The residue was chromatographed using a 70:30 mixture of hexanes: ethyl acetate to give 39 (230 mg) in 35% yield; mp 151–153° C.; IR (KBr) 2962, 1608, 1573, 1508, 1416, 1330, 1275, 1254 cm$^{-1}$; $^1$H NMR ($CDCl_3$) δ3.98 (3H, s), 3.99 (3H, s), 4.01 (3H, s), 5.20 (2H. s), 6.94 (1H, s), 7.10 (1H, s), 7.14 (1H, s), 7.18 (1H, dd, $J_1$=8.4, $J_2$=1.8), 7.36–7.43 (5H, m), 7.54 (1H, d, J=1.5), 7.56 (1H, s), 7.68 (1H, d, J=8.3); $^{13}$C NMR δ56.37, 56.95, 71.69, 106.69, 106.99, 108.67, 116.35, 124.91, 125.78, 127.00, 128.00, 128.87, 129.00, 129.23, 129.53, 131.81, 134.49, 136.15, 141.89, 148.95, 150.41, 151.85; HRMS (EI) calcd for $C_{26}H_{23}NO_6$ m/z: 445.1525; found: 445.1355.

f. 6-(2-Amino-5-benzyloxy-4-methoxyphenyl)-2,3-dimethoxy-naphthalene (41)

Compound 39 (50 mg, 0.112 mmol) was hydrogenated in ethyl acetate (40 mL) at 30 lb./sq. in. using 10% palladium on carbon (15 mg) as catalyst for 16 hours. The solution was passed through a Celite bed and the catalyst was washed with ethyl acetate (10 mL×3). Concentration of the ethyl acetate solution in vacuo gave a crude product. Column chromatography was performed using a 35:65 mixture of hexanes:ethyl acetate as eluting solvent to give two compounds. The compound having the higher $R_f$ material on thin layer chromatography was isolated as compound 41 (34 mg, 73%); IR (KBr) 3446, 2932, 1610, 1509, 1461, 1421, 1254 cm$^{-1}$; $^1$H NMR ($CDCl_3$) δ3.90 (3H, s), 4.01 (3H, s), 4.02 (3H, s), 5.08 (2H. s), 6.42 (1H, s), 6.87 (1H, s), 7.12 (1H, s), 7.15 (1H, s), 7.33–7.48 (6H, m), 7.71–7.75 (2H, m); $^{13}$C NMR δ56.40, 56.42, 56.48, 73.07, 101.48, 106.59, 106.78, 119.09, 119.96, 126.24, 126.78, 127.29, 128.16, 128.20, 128.45, 128.90, 129.86, 135.56, 138.19, 138.88, 141.70, 150.07, 150.30, 150.92; HRMS (EI) calcd for $C_{26}H_{25}NO_4$ m/z: 415.1784; found: 415.1775.

The compound having the lower $R_f$ was isolated as 6-(2-Amino-5-hydroxy-4-methoxyphenyl)-2,3-dimethoxynaphthalene (40) (6 mg, 16%); IR (KBr) 3432, 2937, 2364, 1625, 1508, 1459, 1252, 1232 cm$^{-1}$; UV (MeOH) 238, 208 nm; $^1$H NMR ($CDCl_3$) δ3.88 (3H, s), 4.01 (3H, s), 4.02 (3H, s), 6.40 (1H, s), 6.85 (1H, s), 7.12 (1H, s), 7.15 (1H, s), 7.41 (1H, dd, $J_1$=8.4, $J_2$=1.7); 7.73 (1H, d, J=1.5), 7.74 (1H, d, J=8.3); $^{13}$C NMR δ56.40, 100.47, 106.59, 106.82, 116.90, 121.07, 126.29, 126.83, 127.25, 128.47, 129.85, 135.50, 137.17, 139.05, 147.11, 150.06, 150.27.

EXAMPLE 8

2-Methoxy-8,9-methylenedioxydibenzo[c,h]cinnoline (43)

6-(2-Amino-4,5-methylenedioxyphenyl)-2-methoxynaphthalene 46 (170 mg, 0.58 mmol) was dissolved in acetic acid (4.5 mL) and concentrated hydrochloric acid (0.9 mL). The solution was cooled in an ice bath and diazotized by the dropwise addition of a solution of sodium nitrite (0.36 g in 3.6 mL water). The resulting diazonium solution was allowed to warm slowly to room temperature and left for 1 day. To the resulting red solution containing some precipitate was added 50 mL water and the mixture was extracted with ethyl acetate (30 mL×3). The organic layers were combined and washed with diluted sodium hydroxide solution first, then with water and brine. The organic layer was dried over anhydrous sodium sulfate and evaporated in vacuo. The crude product was purified by column chromatography on silica gel using 50:50 hexanes:ethyl acetate to give the pure 43 (20 mg) in 11% yield; mp 258–260° C.; IR (KBr) 2922, 1611, 1497, 1465, 1414, 1370, 1272, 1201 cm$^{-1}$; UV (MeOH) 286, 228 nm (log $\epsilon$=4.72, 4.41); $^1$H NMR (CDCl$_3$) $\delta$4.01 (3H, s), 6.23 (2H, s), 7.30 (1H, J=2.6), 7.48 (1H, dd, J$_1$=9.1, J$_2$=2.6), 7.75 (1H, s), 7.95 (1H, s), 8.00 (1H, d, J=9.2), 8.19 (1H, d, J=9.1), 9.62 (1H, d, J=9.2); $^{13}$C NMR $\delta$56.01, 97.95, 102.88, 107.48, 108.31, 119.09, 119.61, 119.71, 120.57, 125.89, 126.56, 132.26, 134.59, 142.52, 145.88, 150.21, 152.14, 160.16; HRMS (EI) calcd for C$_{18}$H12N$_2$O$_3$ m/z: 304.0848; found: 304.0843.

The intermediate compound 46 was prepared as follows.
a. 6-(4,5-Methylenedioxy-2-nitrophenyl)-2-methoxynaphthalene (45)

Tetrakis(triphenylphosphine)palladium (0) (120 mg) and cuprous bromide (20 mg) were added to a solution of 2-bromo-6-methoxynaphthalene (0.3 g, 1.27 mmol) and trimethyl(3,4-methylenedioxy-6-nitrophenyl)stannane, 62, (0.45 g, 1.37 mmol) in THF (30 mL) at room temperature and stirred for 0.5 h. The mixture was then refluxed under N$_2$ for 16 h. After cooling, THF was evaporated and 50 mL ethyl acetate was added to the residue. The solution was washed with water. The organic layer was separated and passed through a Celite bed to remove suspended particles. The organic layer was then washed with brine, dried (anhydrous Na$_2$SO$_4$), and evaporated in vacuo. The residue was chromatographed using a 80:20 mixture of hexanes:ethyl acetate to give the desired product 45 (0.29 g) in 71% yield; mp 165–167° C.; IR (KBr) 2911, 1609, 1520, 1482, 1429, 1393, 1344, 1257, 1199 cm$^{-1}$; 1H NMR (CDCl3) $\delta$3.94 (3H, s), 6.14 (2H, s), 6.88 (1H, s), 7.16–7.21 (2H, m), 7.31 (1H, dd, J$_1$=8.5, J$_2$=1.9), 7.47 (1H, s), 7.67–7.77 (3H, m); $^{13}$C NMR $\delta$55.89, 103.45, 105.92, 106.19, 111.69, 119.86, 126.90, 127.02, 127.55, 129.23, 130.09, 133.76, 133.85, 134.48, 143.38, 147.52, 151.47, 158.62; HRMS (EI) calcd for C$_{18}$H$_{13}$NO$_5$ m/z: 323.0794; found: 323.0788.
b. 6-(2-Amino-4,5-methylenedioxyphenyl)-2-methoxynaphthalene (46)

6-(4,5-Methylenedioxy-2-nitrophenyl)-2-methoxynaphthalene 45 (260 mg, 0.81 mmol) was hydrogenated overnight in ethyl acetate (35 mL) at 40–45 lb./sq. in. using 10% palladium on carbon (70 mg) as catalyst. The reaction solution was passed through a Celite bed and the catalyst was washed with ethyl acetate (10 mL×3). Concentration of the ethyl acetate solution in vacuo gave the crude product. The residue was chromatographed using a 75:25 mixture of hexanes:ethyl acetate to give 46 (180 mg) in 76% yield; mp 130–132° C.; IR (KBr) 3463, 3372, 2874, 1631, 1494, 1441, 1389, 1260, 1187cm$^{-1}$; UV (MeOH) 234 nm (log $\epsilon$=4.73); 1H NMR (CDCl3) $\delta$3.56 (2H, s), 3.95 (3H, s), 5.92 (2H, s), 6.40 (1H, s), 6.75 (1H, s), 7.17–7.22 (2H, m), 7.51 (1H, dd, J$_1$=8.5, J$_2$=1.6), 7.73–7.82 (3H, m); 13C NMR $\delta$55.84, 98.33, 101.25, 106.11, 110.71, 119.66, 120.30, 127.79, 128.27, 128.61, 129.60, 129.91, 133.95, 135.11, 138.95, 141.17, 148.05, 158.29; HRMS (EI) calcd for C$_{18}$H$_{15}$NO$_3$ m/z: 293.1052; found: 293.1051.

The intermediate compound 62 was prepared as follows.
c. Trimethyl(3,4-methylenedioxy-6-nitrophenyl)stannane (62)

A mixture of hexamethylditin (1 g, 3.1 mmol), compound 16 (0.7 g, 2.9 mmol) and tetrakis(triphenylphosphine)palladium (100 mg) in anhydrous THF (20 ml) was heated to reflux under nitrogen for 10 h. After cooling to room temperature, THF was evaporated and methylene chloride (30 mL) was added to the residue. To this mixture, aqueous potassium fluoride (7.0M, 1 mL) was added dropwise with vigorous stirring. The mixture was passed through a Celite bed and the filtrate was washed with brine. The methylene chloride layer was dried (anhydrous Na$_2$SO$_4$), filtered and evaporated in vacuo. The residue was chromatographed using 95:5 hexanes:ethyl acetate to give 62 (0.5 g) in 54% yield; $^1$H NMR (CDCl$_3$) $\delta$0.32 (9H, s), 6.12 (2H, s), 7.04 (1H, s), 7.82 (1H, s); $^{13}$C NMR (CDCl$_3$) $\delta$–6.94, 103.27, 105.82, 114.76, 137.19, 147.90, 149.36, 153.36; HRMS (EI) calcd for C$_{10}$H$_{13}$NO$_4$Sn—CH$_3$ m/z: 315.9632; found: 315.9638.

EXAMPLE 9
3-Methoxy-8,9-methylenedioxydibenzo[c,h]cinnoline (44)

7-(2-Amino-4,5-methylenedioxyphenyl)-2-methoxynaphthalene 49 (70 mg, 0.24 mmol) was dissolved in acetic acid (2.0 mL) and concentrated hydrochloric acid (0.4 mL). The solution was cooled in an ice bath and diazotized by the dropwise addition of a solution of sodium nitrite (0.16 g in 1.6 mL water). The resulting diazonium solution was allowed to warm slowly to room temperature and left overnight. To the resulting red solution containing some precipitate was added 50 mL water and the reaction mixture was extracted with ethyl acetate (30 mL×3). The organic layers were combined and washed with diluted sodium hydroxide solution first, then with water and brine. The organic layer was dried over anhydrous sodium sulfate and evaporated in vacuo. The crude product was purified by column chromatography on silica gel using 55:45 hexanes:ethyl acetate to give compound 44 (60 mg 83%); mp 259–261° C.; IR (KBr) 2923, 1612, 1498, 1468, 1234, 1199 cm$^{-1}$; UV (MeOH) 270, 250, 228 nm (log $\epsilon$=4.68, 4.37, 4.44); $^1$H NMR (CDCl$_3$) $\delta$4.12 (3H, s), 6.24 (2H, s), 7.37 (1H, dd, J$_1$=8.8, J$_2$=2.7), 7.80 (1H, s), 7.88 (1H, d, J=8.8), 7.96 (1H, s), 8.03 (1H, d, J=9.1), 8.09 (1H, d, J=9.0), 9.15 (1H, d, J=2.7); $^{13}$C NMR $\delta$56.32, 98.31, 102.93, 104.03, 107.49, 116.36, 120.40, 120.50, 121.09, 127.96, 130.00, 132.54, 133.34, 141.99, 146.10, 150.53, 152.09, 160.28; HRMS (EI) calcd for C$_{18}$H$_{12}$N$_2$O$_3$ m/z: 304.0848; found: 304.0852.

The intermediate compound 49 was prepared as follows.
a. 7-Methoxy-2-trifluoromethanesulfonyloxynaphthalene (47)

A solution of 7-methoxy-2-naphthol (0.75 g, 4.3 mmol) in THF (10 mL) was added to a suspension of sodium hydride (60 wt %, 205 mg, 5.1 mmol) in THF (10 mL) cooled by ice bath and stirred for 1.5 h. A solution of N-phenyltrifluoromethanesulfonimide (1.55 g, 4.34 mmol) in THF (10 mL) was then added, and the reaction mixture was stirred for 9 h. After evaporation of the solvent in vacuo, the residue was mixed with silica gel (4 g) and then chromatographed using 500:18 hexanes:ethyl acetate to give pure 47 (1.19 g) in 90% yield; mp 34° C. (lit[100] 34° C.); $^1$H NMR (CDCl$_3$) 3.93 (3H, s), 7.13–7.25 (3H, m), 7.65 (1H, d, J=1.5), 7.77 (1H, d, J=9.1), 7.83 (1H, d, J=8.8); 13C NMR $\delta$55.88, 106.25, 116.13, 117.49, 118.52, 120.75, 122.51, 128.34, 129.87, 130.72, 135.41, 148.29, 159.39; HRMS (EI) calcd for C$_{12}$H$_9$SO$_4$F$_3$ m/z: 306.0174; found: 306.0176.

b. 7-(4,5-Methylenedioxy-2-nitrophenyl)-2-methoxynaphthalene (48)

Tetrakis(triphenylphosphine)palladium (0) (120 mg) and cuprous bromide (20 mg) were added to a solution of 7-Methoxy-2-trifluoromethanesulfonyloxynaphthalene 47 (336 mg, 1.1 mmol) and trimethylnitroarylstannane 62 (300 mg, 0.92 mmol) in THF (30 mL) at room temperature and stirred for 0.5 h. The mixture was then refluxed under $N_2$ overnight. After cooling, THF was evaporated in vacuo and ethyl acetate (30 mL) was added to the residue. The solution was washed with water. The organic layer was separated and passed through a Celite bed to remove suspended particles. The organic layer was then washed with brine, dried (anhydrous $Na_2SO_4$), and evaporated in vacuo. The residue was chromatographed using a 80:20 mixture of hexanes: ethyl acetate to give 48 (100 mg) in 34% yield; IR (KBr) 2915, 1627, 1509, 1481, 1425, 1333, 1262, 1218 cm$^{-1}$; 1H NMR (CDCl3) δ3.92 (3H, s), 6.15 (2H, s), 6.88 (1H, s), 7.13–7.23 (3H, m), 7.48 (1H, s), 7.64 (1H, s), 7.74–7.81 (2H, m); 13C NMR δ55.81, 103.47, 105.90, 106.46, 111.60, 119.84, 124.13, 126.07, 128.50, 128.72, 129.75, 133.89, 134.97, 136.60, 143.42, 147.63, 151.45, 158.61; HRMS (EI) calcd for $C_{18}H_{13}NO_5$ m/z: 323.0794; found: 323.0787.

c. 7-(2-Amino-4,5-methylenedioxyphenyl)-2-methoxynaphthalene (49)

7-(4,5-Methylenedioxy-2-nitrophenyl)-2-methoxynaphthalene 48 (100 mg, 0.31 mmol) was hydrogenated overnight in ethyl acetate (35 mL) at 40–45 lb./sq. in. using 10% palladium on carbon (30 mg) as catalyst. The reaction solution was passed through a Celite bed and the catalyst was washed with ethyl acetate (10 mL×3). The ethyl acetate solution was concentrated in vacuo gave the crude product. The residue was chromatographed using a 75:25 mixture of hexanes:ethyl acetate to give 49 (75 mg) in 83% yield; IR (KBr) 3426, 3366, 2364, 2339, 1629, 1503, 1487, 1467, 1233, 1215, 1187 cm$^{-1}$; 1H NMR (CDCl$_3$) δ3.64 (2H, s), 3.94 (3H, s), 5.92 (2H, s), 6.40 (1H, s), 6.76 (1H, s), 7.15–7.20 (2H, m), 7.40 (1H, dd, $J_1$=8.3, $J_2$=1.7), 7.75–7.85 (3H, m); 13C NMR δ55.83, 98.35, 101.27, 106.25, 110.65, 119.35, 120.29, 125.82, 127.35, 128.31, 128.72, 129.67, 135.34, 137.99, 138.99, 141.17, 148.16, 158.49; HRMS (EI) calcd for $C_{18}H_{15}NO_3$ m/z: 293.1052; found: 293.1052.

EXAMPLE 10

3-Methoxy-8,9-methylenedioxydibenzo [c,h]cinnoline (44)

The compound of Example 9 (compound 44) was also prepare as follows. Lithium aluminum hydride (46 mg, 1.2 mmol) was added to a stirred solution of compound 54 (74 mg, 0.2 mmol) in diethyl ether (10 mL) and benzene (10 mL). The mixture was stirred under reflux for 1 h. After cooling to room temperature, the excess hydride was decomposed with 0.05 mL water, 0.05 mL 15% NaOH and 0.15 mL water, and the reaction mixture filtered through a Celite bed. Evaporation of solvent in vacuo gave the crude product, which was purified by column chromatography using 50:50 hexanes:ethyl acetate mixture as eluting solvent to provide compound 44 (46 mg,75%).

The intermediate compound 54 was prepared as follows.

a. 4-Methyl-2,3,4,5-tetrabromophenol (50)

p-Cresol (5 g, 46 mmol) was added dropwise to 15 mL (0.29 mol) of bromine containing 0.25 g Fe filings at room temperature. During the addition of p-cresol, small portions of chloroform were added from time to time to facilitate stirring. After 6 h, HBr evolution subsided. The residue was dissolved in hot chloroform, washed with aqueous $Na_2S_2O_3$, $NaHCO_3$ dried with anhydrous sodium sulfate and evaporated in vacuo. The crude product was purified by column chromatography using a 95:5 mixture of hexanes and ethyl acetate to give 3.57 g of 50 (92% yield); mp 195–196° C. (lit$^{93}$ 196° C.); 1H NMR (acetone-d6) δ2.71 (3H, s); 13C NMR δ28.10, 115.20, 127.66, 133.24, 152.19.

b. 4-Methyl-4-nitro-2,3,5,6-tetrabromo-2,5-cyclohexadien-1-one (51)

A solution containing 1.6 mL of nitric acid (d=1.52, 70%) in 10 mL of acetic acid was added over a 10 minute period to a solution of compound 50 (3.2 g, 7.6 mmol) in 25 mL of pure acetic acid at about 10° C. The reaction mixture was stirred for 4 h and 30 mL of water was then added. The precipitates were filtered and washed with water and heptane and dried in vacuum to give 2.9 g of pure 51 (82% yield); 1H NMR (CDCl3) δ2.26 (3H, s); IR (KBr) 1680 (C=O) (lit$^{93}$).

c. 2-Hydroxy-7-methoxy-1-nitronaphthalene (52)

7-Methoxy-2-naphthol (871 mg, 5 mmol) was dissolved in 40 mL of dry ether. To this solution was added 51 (2.33 g, 5 mmol) as a solid. The color of the solution slowly became red, and eventually dark red with some dark precipitate adhering to the inside surface of the flask. The reaction continued for 2.5 h at room temperature. Evaporation of the solvent gave the crude product. To the residue was added 20 mL of methanol/water (80/20). The reaction mixture was filtered and washed with methanol/water (80/20). The filtrate was then evaporated under vacuum and purified using column. A 90:10 mixture of hexanes and ethyl acetate was used as the eluting solvent. The yield was of 380 mg 52 (35%); mp 130–131° C. (lit$^{93}$ 130° C.); 1H NMR (CDCl3) δ3.96 (3H, s), 7.04 (1H, d, J=9.0), 7.10 (1H, dd, J=9.0, J=2.6), 7.67 (1H, d, J=8.9), 7.87 (1H, d, J=8.9), 8.37 (1H, d, J=2.5); 13C NMR δ56.03, 104.30, 116.80, 117.28, 124.22, 129.35, 131.52, 139.59, 160.41, 162.75.

d. 7-Methoxy-1-nitro-2-trifluoromethanesulfonyloxynaphthalene (53)

A solution of compound 52 (380 mg, 2.24 mmol) in THF (15 mL) was added to a suspension of sodium hydride (60 wt % in mineral oil, 90 mg, 2.25 mmol) in THF (10 mL) cooled in an ice bath and stirred for 0.5 h. A solution of N-phenyltrifluoromethanesulfonimide (800 mg, 2.24 mmol) in THF (10 mL) was then added, and the reaction stirred at 0° C. for 8 h. After concentration in vacuo, the residue was chromatographed using 85:15 hexanes:ethyl acetate to give triflate 53 (526 mg) containing approximately 10% N-phenyltrifluoromethanesulfonamide.

e. 6-(4,5-Methylenedioxy-2-nitrophenyl)-2,3-dimethoxy-5-nitronaphthalene (54)

Tetrakis(triphenylphosphine)palladium (0) (100 mg) and cuprous bromide (20 mg) was added to a solution of 7-Methoxy-1-nitro-2-trifluoromethanesulfonyloxynaphthalene 53 (366 mg, 1.04 mmol) and trimethylnitroarylstannane 62 (500 mg, 1.52 mmol) in THF (30 mL) at room temperature and stirred for 0.5 h. The mixture was then refluxed under $N_2$ overnight. After cooling, THF was evaporated and ethyl acetate (30 mL) was added to the residue. The solution was washed with water. The organic layer was separated and passed through a Celite bed to remove suspended particles. The organic layer was then washed with brine, dried (anhydrous $Na_2SO_4$), and evaporated in vacuo. The residue was chromatographed using a 70:30 mixture of hexanes:ethyl acetate to give 54 (160 mg) in 42% yield; mp 187–189° C.; IR (KBr) 2925, 1628, 1526, 1487, 1364, 1332, 1265, 1230 cm$^{-1}$; 1H NMR (CDCl3) δ3.92 (3H, s), 6.19 (2H, d), 6.76 (1H, s), 7.12 (1H, d, J=2.5), 7.18 (1H, d, J=8.3), 7.28 (1H, dd, $J_1$=9.0, $J_2$=2.3), 7.70 (1H, s), 7.85 (1H, d, J=9.2), 7.93 (1H, d, J=8.4), 13C NMR δ56.08, 100.59, 103.93, 106.31, 110.70, 121.54, 124.07, 126.47, 128.71, 129.55, 130.33, 130.99, 131.23, 142.83, 148.92, 152.07, 160.68.

EXAMPLE 10

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

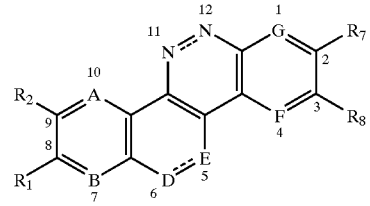

wherein:
A is N or $CR_3$;
B is N or $CR_s$;
D is $NR_e$ or $CR_aR_b$;
E is $NR_f$ or $CR_cR_d$;
F is N or $CR_i$;
G is N or $CR_6$;
$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;
$R_6$, $R_7$ and $R_8$ are each individually hydrogen, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;
each bond represented by—is individually present or absent;
$R_a$ and $R_b$ are each independently hydrogen or $(C_1-C_6)$alkyl if the bond between the 5- and 6-positions represented by—is absent; or $R_a$ is hydrogen or $(C_1-C_6)$alkyl and $R_b$ is absent if the bond between the 5- and 6-positions represented by—is present;
$R_c$ and $R_d$ are each independently hydrogen or $(C_1-C_6)$alkyl if the bond between the 5- and 6-positions represented by—is absent; or $R_c$ is hydrogen or $(C_1-C_6)$alkyl and $R_d$ is absent if the bond between the 5- and 6-positions represented by—is present;
$R_e$ is hydrogen or $(C_1-C_6)$alkyl if the bond between the 5- and 6-positions represented by—is absent; or $R_e$ is absent if the bond between the 5- and 6-positions represented by—is present;
$R_f$ is hydrogen or $(C_1-C_6)$alkyl if the bond between the 5- and 6-positions represented by—is absent; or $R_f$ is absent if the bond between the 5- and 6-positions represented by—is present;
each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and
each $R_m$ is independently $(C_1-C_6)$alkanoyl, aryl, or aryl $(C_1-C_6)$alkyl;
each $R_s$ and $R_t$ is independently hydrogen, methyl, nitro, hydroxy, amino, or halo;
wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or
$R_n$ and $R_p$ together with the nitrogen to which they are attached are pyrrolidino, piperidino, morpholino, or thiomorpholino;
wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;
and wherein the nitrogens at the 11-position and the 12-position are each substituted with a hydrogen substituent when the bond between the 11-position and the 12-position represented by—is absent;
provided no more than two of A–G comprise nitrogen;
provided $R_1-R_3$ and $R_6-R_8$ are not each hydrogen;
provided the compound of formula (I) is not 2,3,8,9-tetramethoxy-5,6-diazachrysene or 2,3-8,9-bismethylenedioxy-5,6-diazachrysene; and
provided the compound of formula (I) is not a compound of formula (I) wherein D is $NR_e$; when A $CR_3$; B is $CR_s$; E is $CR_cR_d$; F is $CR_t$; and G is $CR_6$;
or a pharmaceutically acceptable salt thereof.

2. The compound of claim 1 wherein $R_3$ is hydrogen.

3. The compound of claim 1 wherein $R_1$, $R_2$ and $R_3$ are each individually hydrogen, or $(C_1-C_6)$alkoxy; or $R_1$ and $R_2$ taken together are methylenedioxy and $R_3$ is hydrogen or $(C_1-C_6)$alkoxy.

4. The compound of claim 1 wherein $R_7$ and $R_8$ taken together are methylenedioxy.

5. The compound of claim 1 wherein $R_2$ is hydrogen, methyl, nitro, hydroxy, amino, fluoro or chloro.

6. The compound of claim 1 wherein $R_8$ is hydrogen, nitro, hydroxy, amino, fluoro or chloro.

7. The compound of claim 1 wherein the bonds represented by—are both present.

8. The compound of claim 1 wherein $R_1$ is $(C_1-C_6)$alkoxy, nitro, hydroxy, or halo; or $R_1$ and $R_2$ taken together are methylenedioxy.

9. The compound of claim 1 wherein $R_2$ is $(C_1-C_6)$alkoxy, nitro, hydroxy, or halo; or a pharmaceutically acceptable salt thereof.

10. The compound of claim 1 wherein $R_3$ is $(C_1-C_6)$ alkoxy, nitro, hydroxy, or halo; or $R_2$ and $R_3$ taken together are methylenedioxy.

11. The compound of claim 1 wherein $R_7$ is $(C_1-C_6)$ alkoxy, nitro, hydroxy, or halo.

12. The compound of claim 1 wherein $R_6$ is $(C_1-C_6)$ alkoxy, nitro, hydroxy, or halo; or $R_6$ and $R_7$ taken together are methylenedioxy.

13. The compound 2,3-Dimethoxy-dibenzo[c,h]cinnoline (6); 2,3-Dimethoxy-8,9-methylenedioxy-dibenzo[c,h] cinnoline (14); 2,3,8-Trimethoxydibenzo[c,h]cinnoline (60); 2,3,9-Trimethoxydibenzo[c,h]cinnoline (61); 9-Benzyloxy-2,3,8-trimethoxydibenzo[c,h]cinnoline (42); 2-Methoxy-8,9-methylenedioxydibenzo[c,h]cinnoline (43); or 3-Methoxy-8,9-methylenedioxydibenzo[c,h]cinnoline (44); or a pharmaceutically acceptable salt thereof.

14. The compound 2,3-Dimethoxy-8,9-methylenedioxy-dibenzo[c,h]cinnoline (14); or a pharmaceutically acceptable salt thereof.

15. The compound of claim 1 wherein one of $R_2$ and $R_8$ is hydrogen, nitro, hydroxy, amino, fluoro or chloro; or at least one of $R_2$ and $R_8$ forms part of a methylenedioxy.

16. A pharmaceutical composition comprising an effective amount of a compound of formula I:

wherein:
A is N or $CR_3$;
B is N or $CR_s$;
D is $NR_e$ or $CR_aR_b$;
E is $NR_f$ or $CR_cR_d$;
F is N or $CR_t$;
G is N or $CR_6$;
$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;
$R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;
each bond represented by—is individually present or absent;
$R_a$ and $R_b$ are each independently hydrogen or $(C_1-C_6)$ alkyl if the bond between the 5- and 6-positions represented by—is absent; or $R_a$ is hydrogen or $(C_1-C_6)$ alkyl and $R_b$ is absent if the bond between the 5- and 6-positions represented by—is present;
$R_c$ and $R_d$ are each independently hydrogen or $(C_1-C_6)$ alkyl if the bond between the 5-and 6-positions represented by—is absent; or $R_c$ is hydrogen or $(C_1-C_6)$ alkyl and $R_d$ is absent if the bond between the 5- and 6-positions represented by—is present;
$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl;

each $R_m$ is independently $(C_1-C_6)$alkanoyl, aryl, or aryl $(C_1-C_6)$alkyl; and each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided $R_1-R_3$ and $R_6-R_8$ are not each hydrogen;

provided the compound is not 9-hydroxy-2,3,8-trimethoxy-dibenzo[c,h]cinnoline;

provided the compound of formula (I) is not a compound of formula (I) wherein D is $NR_e$; when A $CR_3$; B is $CR_s$; E is $CR_cR_d$; F is $CR_t$; and G is $CR_6$;

or a pharmaceutically acceptable salt thereof; in combination with a pharmaceutically acceptable diluent or carrier.

17. A compound of formula I:

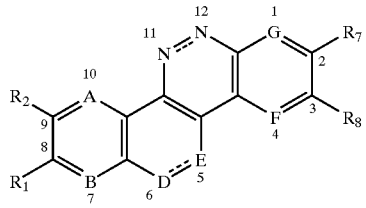

wherein:

A is N or $CR_3$;

B is N or $CR_s$;

D is $NR_e$ or $CR_aR_b$;

E is $NR_f$ or $CR_cR_d$;

F is N or $CR_t$;

G is N or $CR_6$;

$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;

for $R_6$, $R_7$ and $R_8$ either:

a) $R_6$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo, $R_7$ is $(C_1-C_6)$alkoxy, and $R_8$ is hydrogen $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;

b) $R_6$ and $R_7$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo, or $R_6$ and $R_7$ taken together are methylenedioxy, and $R_8$ is $(C_1-C_6)$alkoxy; or c) $R_6$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; and $R_7$ and $R_8$ taken together are methylenedioxy;

each bond represented by—is individually present or absent;

$R_a$ and $R_b$ are each independently hydrogen or $(C_1-C_6)$ alkyl if the bond between the 5- and 6-positions represented by—is absent; or $R_a$ is hydrogen or $(C_1-C_6)$ alkyl and $R_b$ is absent if the bond between the 5- and 6-positions represented by—is present;

$R_c$ and $R_d$ are each independently hydrogen or $(C_1-C_6)$ alkyl if the bond between the 5- and 6-positions represented by—is absent; or $R_c$ is hydrogen or $(C_1-C_6)$ alkyl and $R_d$ is absent if the bond between the 5- and 6-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided the compound of formula (I) is not 2,3,8,9-tetramethoxy-5,6-diazachrysene or 2,3-8,9-bismethylenedioxy-5,6-diazachrysene; and provided the compound of formula (I) is not a compound of formula (I) wherein D is $NR_e$; when A $CR_3$; B is $CR_s$; E is $CR_cR_d$; F is $CR_t$; and G is $CR_6$;

or a pharmaceutically acceptable salt thereof.

18. A compound of formula I:

[I]

wherein:

A is N or $CR_3$;

B is N or $CR_s$;

D is $NR_e$ or $CR_aR_b$;

E is $NR_f$ or $CR_cR_d$;

F is N or $CR_t$;

G is N or $CR_6$;

$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

for $R_6$, $R_7$ and $R_8$ either:
  a) $R_6$ and $R_7$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo, and $R_8$ is $C_1-C_6$)alkoxy, nitro, hydroxy, or halo; or
  b) $R_6$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; and $R_7$ and $R_8$ taken together are methylenedioxy;

each bond represented by—is individually present or absent;

$R_a$ and $R_b$ are each independently hydrogen or $(C_1-C_6)$alkyl if the bond between the 5- and 6-positions represented by—is absent; or $R_a$ is hydrogen or $(C_1-C_6)$alkyl and $R_b$ is absent if the bond between the 5- and 6-positions represented by—is present;

$R_c$ and $R_d$ are each independently hydrogen or $(C_1-C_6)$alkyl if the bond between the 5- and 6-positions represented by—is absent; or $R_c$ is hydrogen or $(C_1-C_6)$alkyl and $R_d$ is absent if the bond between the 5- and 6-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo; wherein any $(C_1-C_6)$alkyl, $(C_3-C_6)$cycloalkyl, or $(C_1-C_6)$alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_6)$alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided the compound of formula (I) is not 2,3,8,9-tetramethoxy-5,6-diazachrysene or 2,3-8,9-bismethylenedioxy-5,6-diazachrysene; and provided the compound of formula (I) is not a compound of formula (I) wherein D is $NR_e$; when A $CR_3$; B is $CR_s$; E is $CR_cR_d$; F is $CR_t$; and G is $CR_6$;

or a pharmaceutically acceptable salt thereof.

19. A compound of formula II:

II wherein:

$R_1$ and $R_2$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_g$, $C(=O)R_k$, $COOR_k$, $OR_m$, or halo;

each bond represented by—is individually present or absent;

$R_a$ and $R_b$ are each independently hydrogen or $(C_1-C_6)$ alkyl if the bond represented by—is absent; or $R_a$ is hydrogen or $(C_1-C_6)$alkyl and $R_1$, is absent if the bond represented by—is present;

$R_c$ and $R_d$ are each independently hydrogen or $(C_1-C_6)$ alkyl if the bond represented by—is absent; or $R_c$ is hydrogen or $(C_1-C_6)$alkyl and $R_d$ is absent if the bond represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

20. A compound of formula III:

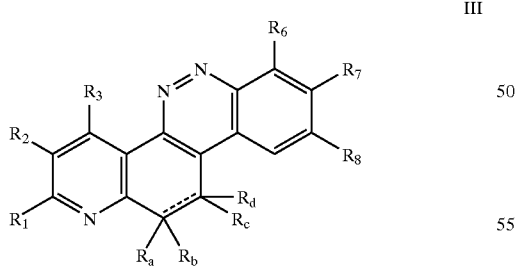

III wherein:

$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;

$R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$ alkyl if the bond represented by—is absent; or $R_a$ is hydrogen or $(C_1-C_6)$alkyl and $R_b$ is absent if the bond represented by—is present;

$R_c$ and $R_d$ are each independently hydrogen or $(C_1-C_6)$ alkyl if the bond represented by—is absent; or $R_c$ is hydrogen or $(C_1-C_6)$alkyl and $R_d$ is absent if the bond represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

21. A compound of formula V:

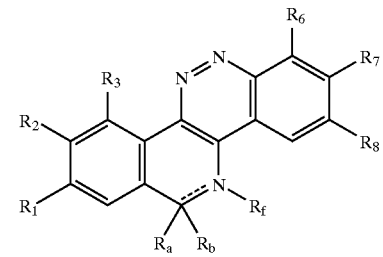

V wherein:

$R_1$, $R_2$ and $R_3$ are each individually hydrogen, $(C_1-C_6)$ alkyl, $(C_3-C_6)$cycloalkyl, $(C_1-C_1)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

each bond represented by—is individually present or absent;

$R_a$ and $R_b$ are each independently hydrogen or $(C_1-C_6)$alkyl if the bond represented by—is absent; or $R_a$ is hydrogen or $(C_1-C_6)$alkyl and $R_b$ is absent if the bond represented by—is present;

$R_f$ is hydrogen or $(C_1-C_6)$alkyl if the bond represented by—is absent; or $R_f$ is absent if the bond represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_1)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

22. A compound of formula VI:

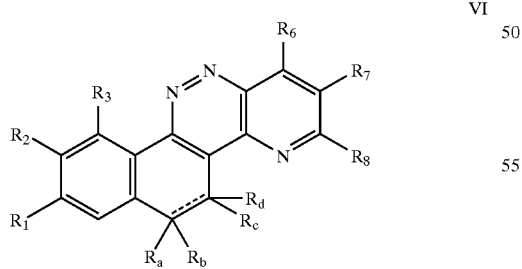

VI wherein:

$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$ are each individually hydrogen, $C_1-C_6$alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$alkyl if the bond represented by—is absent; or $R_a$ is hydrogen or $(C_1-C_6)$alkyl and $R_b$ is absent if the bond represented by—is present;

$R_c$ and $R_d$ are each independently hydrogen or $(C_1-C_6)$alkyl if the bond represented by—is absent; or $R_c$ is hydrogen or $(C_1-C_6)$alkyl and $R_d$ is absent if the bond represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

23. A compound of formula VII:

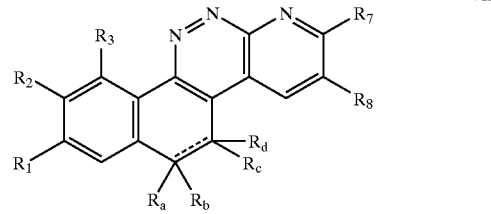

VII wherein:

$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_7$ and $R_8$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

each bond represented by—is individually present or absent;

$R_a$ and $R_b$ are each independently hydrogen or $(C_1-C_6)$ alkyl if the bond represented by—is absent; or $R_a$ is hydrogen or $(C_1-C_6)$alkyl and $R_b$ is absent if the bond represented by—is present;

$R_c$ and $R_d$ are each independently hydrogen or $(C_1-C_6)$ alkyl if the bond represented by—is absent; or $R_c$ is hydrogen or $(C_1-C_6)$alkyl and $R_d$ is absent if the represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$, together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoroethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

24. A compound of formula VIII:

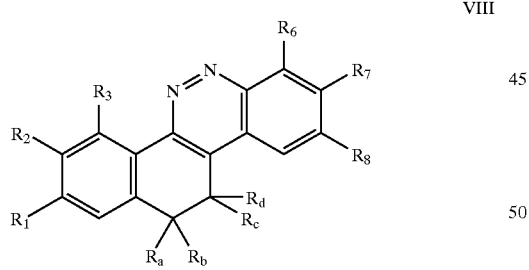

VIII wherein:

$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;

$R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$ alkyl;

$R_c$ and $R_d$ are each independently hydrogen or $(C_1-C_6)$;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

25. A compound of formula IX:

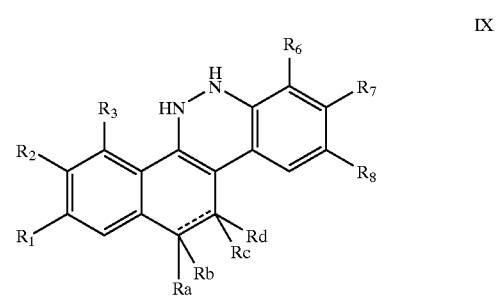

IX wherein:

$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;

$R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$alkyl if the bond represented by—is absent; or $R_a$ is hydrogen or $(C_1-C_6)$alkyl and $R_b$ is absent if the bond represented by—is present;

$R_c$ and $R_d$ are each independently hydrogen or $(C_1-C_6)$alkyl if the bond represented by—is absent; or $R_c$ is hydrogen or $(C_1-C_6)$alkyl and $R_d$ is absent if the bond represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

26. A compound of formula X:

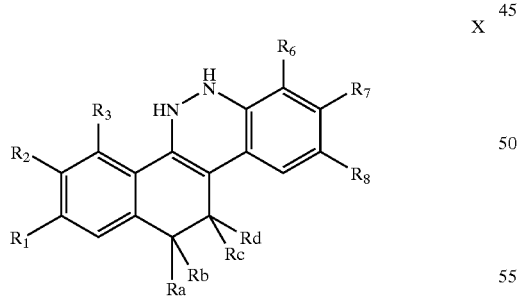

wherein:

$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;

$R_a$ and $R_b$ are each independently hydrogen or $(C_1-C_6)$;

$R_c$ and $R_d$ are each independently hydrogen or $(C_1-C_6)$alkyl;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy; and or a pharmaceutically acceptable salt thereof.

27. A compound of formula I:

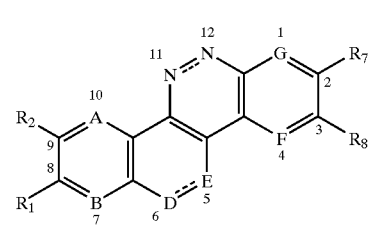

wherein:

A is N or $CR_3$;

B is N or $CR_s$;

D is $NR_e$ or $CR_aR_b$;

E is $NR_f$ or $CR_cR_d$;

F is N or $CR_r$;

G is N or $CR_6$;

$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$ are each individually hydrogen, $(C_3-C_6)$ cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$ alkyl if the bond between the 5- and 6-positions represented by—is absent; or $R_a$ is hydrogen or $(C_1-C_6)$ alkyl and $R_b$ is absent if the bond between the 5- and 6-positions represented by—is present;

$R_c$ and $R_d$ are each independently hydrogen or $(C_1-C_6)$ alkyl if the bond between the 5- and 6-positions represented by—is absent; or $R_c$ is hydrogen or $(C_1-C_6)$ alkyl and $R_d$ is absent if the bond between the 5- and 6-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2 or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoroethoxy, carboxy, amino, $(C_1-C_6)$alkyl, $(C_3-C_6)$ cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided $R_1-R_3$ and $R_6-R_8$ are not each hydrogen;

provided the compound of formula (I) is not 2,3,8,9-tetramethoxy-5,6-diazachrysene or 2,3-8,9-bismethylenedioxy-5,6-diazachrysene; and provided the compound of formula (I) is not a compound of formula (I) wherein D is $NR_e$; when A $CR_3$; B is $CR_s$; F is $CR_cR_d$; F is $CR_i$; and G is $CR_6$;

provided the compound is not 9-hydroxy-2,3,8-trimethoxydibenzo[c,h]cinnoline;

or a pharmaceutically acceptable salt thereof.

28. A pharmaceutical composition comprising a compound of formula I:

wherein:

A is N or $CR_3$;

B is N or $CR_s$,

D is $NR_e$ or $CR_aR_b$;

F is $NR_f$ or $CR_cR_d$;

F is N or $CR_i$;

G is N or $CR_6$;

$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;

$R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$ alkyl if the bond between the 5- and 6-positions represented by—is absent; or $R_a$ is hydrogen or $(C_1-C_6)$ alkyl and $R_b$ is absent if the bond between the 5- and 6-positions represented by—is present;

$R_c$ and $R_d$ are each independently hydrogen or $(C_1-C_6)$ alkyl if the bond between the 5- and 6-positions represented by—is absent; or $R_e$ is hydrogen or $(C_1-C_6)$ alkyl and $R_d$ is absent if the bond between the 5- and 6-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided $R_1-R_3$ and $R_6-R_8$ are not each hydrogen;

provided the compound of formula (I) is not 2,3,8,9-tetramethoxy-5,6-diazachrysene or 2,3-8,9-bismethylenedioxy-5,6-diazachrysene; and provided the compound of formula (I) is not a compound of formula (I) wherein D is $NR_e$; when A $CR_3$; B is $CR_s$; E is $CR_cR_d$; F is $CR_f$; and G is $CR_6$;

or a pharmaceutically acceptable salt thereof;
in combination with a pharmaceutically effective diluent or carrier.

29. A method of inhibiting cancer cell growth, comprising administering to a mammal afflicted with cancer, an amount of a compound of formula I:

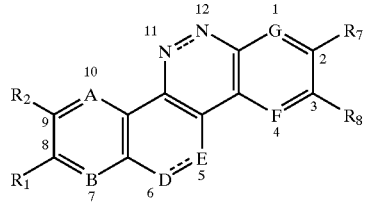

wherein:
A is N or $CR_3$;
B is N or $CR_s$;
D is $NR_e$ or $CR_aR_b$;
E is $NR_f$ or $CR_cR_d$;
F is N or $CR_t$;
G is N or $CR_6$;

$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;

$R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$, is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$ alkyl if the bond between the 5- and 6-positions represented by—is absent; or $R_a$ is hydrogen or $(C_1-C_6)$ alkyl and $R_b$ is absent if the bond between the 5- and 6-positions represented by—is present;

$R_c$ and $R_d$ are each independently hydrogen or $(C_1-C_6)$ alkyl if the bond between the 5- and 6-positions represented by—is absent; or $R_c$ is hydrogen or $(C_1-C_6)$ alkyl and $R_d$ is absent if the bond between the 5- and 6-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R_8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided $R_1-R_3$ and $R_6-R_8$ are not each hydrogen;

provided the compound of formula (I) is not 2,3,8,9-tetramethoxy-5,6-diazachrysene or 2,3-8,9-bismethylenedioxy-5,6-diazachrysene; and provided the compound of formula (I) is not a compound of formula (I) wherein D is $NR_e$; when A $CR_3$; B is $CR_s$; E is $CR_cR_d$; F is $CR_t$; and G is $CR_6$;

or a pharmaceutically acceptable salt thereof;

effective to inhibit the growth of said cancer cells.

30. A method comprising inhibiting cancer cell growth by contacting said cancer cell in vitro or in vivo with an amount of a compound of formula I:

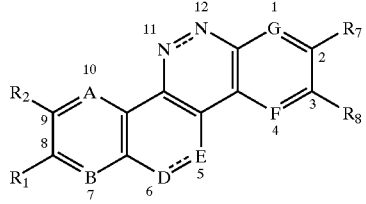

wherein:

A is N or $CR_3$;

B is N or $CR_s$;

D is $NR_e$ or $CR_aR_b$;

E is $NR_f$ or $CR_cR_d$;

F is N or $CR_t$;

G is N or $CR_6$;

$R_1$, $R_2$ and $R_3$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$alkyl if the bond between the 5- and 6-positions represented by—is absent; or $R_a$ is hydrogen or $(C_1-C_6)$alkyl and $R_b$ is absent if the bond between the 5- and 6-positions represented by—is present;

$R_c$ and $R_d$ are each independently hydrogen or $(C_1-C_6)$alkyl if the bond between the 5- and 6-positions represented by—is absent; or $R_c$ is hydrogen or $(C_1-C_6)$alkyl and $R_d$ is absent if the bond between the 5- and 6-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5- and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$alkoxy of $R^1$, $R^2$, $R_3$, $R^6$, $R^7$, $R^8$, or $R_k$ is optionally substituted on carbon with 1, 2 or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one rind is aromatic optionally with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided $R_1-R_3$ and $R_6-R_8$ are not each hydrogen;

provided the compound of formula (I) is not 2,3,8,9-tetramethoxy-5,6-diazachrysene or 2,3-8,9-bismethylenedioxy-5,6-diazachrysene; and provided the compound of formula (I) is not a compound of formula (I) wherein D is $NR_e$; when A $CR_3$; B is $CR_s$; E is $CR_cR_d$; F is $CR_t$; and G is $CR_6$;

or a pharmaceutically acceptable salt thereof;

effective to inhibit the growth of said cancer cell.

31. A method of producing an antibacterial effect in a mammal in need of such treatment, comprising administering to the mammal an amount of a compound of formula I:

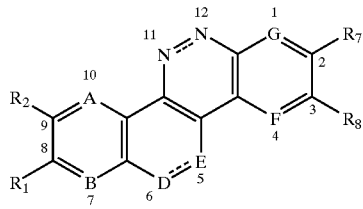

wherein:
A is N or $CR_3$;
B is N or $CR_s$;
D is $NR_e$ or $CR_aR_b$;
E is $NR_f$ or $CR_cR_d$;
F is N or $CR_t$;
G is N or $CR_6$;
$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;
$R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_1-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;
each bond represented by—is individually present or absent;
$R_a$ and $R_b$ are each independently hydrogen or $(C_1-C_6)$ alkyl if the bond between the 5- and 6-positions represented by—is absent; or $R_a$ is hydrogen or $(C_1-C_6)$ alkyl and $R_b$ is absent if the bond between the 5- and 6-positions represented by—is present;
$R_c$ and $R_d$ are each independently hydrogen or $(C_1-C_6)$ alkyl if the bond between the 5- and 6-positions represented by—is absent; or $R_c$ is hydrogen or $(C_1-C_6)$ alkyl and $R_d$ is absent if the bond between the 5- and 6-positions represented by—is present;
$R_e$ is hydrogen or $(C_1-C_6)$alkyl if the bond between the 5- and 6-positions represented by—is absent; or $R_e$ is absent if the bond between the 5- and 6-positions represented by—is present;
$R_f$ is hydrogen or $(C_1-C_6)$alkyl if the bond between the 5- and 6-positions represented by—is absent; or $R_f$ is absent if the bond between the 5- and 6-positions represented by—is present;
each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and
each $R_m$ is independently $(C_1-C_6)$alkanoyl, aryl, or aryl $(C_1-C_6)$alkyl;
each $R_s$ and $R_t$ is independently hydrogen, methyl, nitro, hydroxy, amino, or halo;
wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2 or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;
wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;
and wherein the nitrogens at the 11-position and the 12-position are each substituted with a hydrogen substituent when the bond between the 11-position and the 12-position represented by—is absent;
provided no more than two of A–G comprise nitrogen;
provided $R_1-R_3$ and $R_6-R_8$ are not each hydrogen;
provided the compound of formula (I) is not 2,3,8,9-tetramethoxy-5,6-diazachrysene or 2,3-8,9-bismethylenedioxy-5,6-diazachrysene; and
provided the compound of formula (I) is not a compound of formula (I) wherein D is $NR_e$; when A $CR_3$; B is $CR_s$; E is $CR_cR_d$; F is $CR_t$; and G is $CR_6$;
or a pharmaceutically acceptable salt thereof;
effective to provide an antibacterial effect.

32. A method of producing an antifungal effect in a mammal in need of such treatment comprising administering to the mammal an amount of a compound of formula I:

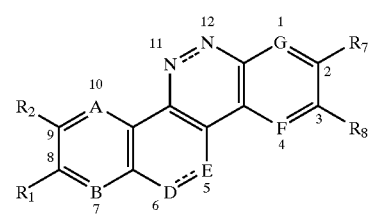

wherein:
A is N or $CR_3$;
B is N or $CR_s$;
D is $NR_e$ or $CR_aR_b$;
E is $NR_f$ or $CR_cR_b$;
F is N or $CR_t$;
G is N or $CR_6$;
$R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;

$R_6$, $R_7$ and $R_8$ are each individually hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_b$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$alkoxy, nitro, hydroxy, $NR_gR_h$, $C(=O)R_k$, $COOR_k$, $OR_m$, or halo;

each bond represented by—is individually present or absent;

$R_a$ and $R_b$ are each independently hydrogen or $(C_1-C_6)$alkyl if the bond between the 5- and 6-positions represented by—is absent; or $R_a$ is hydrogen or $(C_1-C_6)$alkyl and $R_b$ is absent if the bond between the 5- and 6-positions represented by—is present;

$R_c$ and $R_d$ are each independently hydrogen or $(C_1-C_6)$alkyl if the bond between the 5- and 6-positions represented by—is absent; or $R_c$ is hydrogen or $(C_1-C_6)$alkyl and $R_d$ is absent if the bond between the 5- and 6-positions represented by—is present;

$R_e$ is hydrogen or $(C_1-C_6)$alkyl if the bond between the 5- and 6-positions represented by—is absent; or $R_e$ is absent if the bond between the 5- and 6-positions represented by—is present;

$R_f$ is hydrogen or $(C_1-C_6)$alkyl if the bond between the 5-and 6-positions represented by—is absent; or $R_f$ is absent if the bond between the 5- and 6-positions represented by—is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

each $R_s$ and $R_t$ is independently hydrogen, methyl, nitro, hydroxy, amino, or halo;

wherein any $(C_1-C_6)$alkyl, $(C_3-C_6)$cycloalkyl, or $(C_1-C_6)$alkoxy of $R^1$, $R^2$, $R^3$, $R^6$, $R^7$, $R^8$, or $R_k$ is optionally substituted on carbon with 1, 2 or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$alkanoyl; or $R_n$ and $R_p$ together with the nitrogen to which they are attached are pyrrolidino, piperidino, morpholino, or thiomorpholino;

wherein any aryl is a phenyl radical or an ortho-fused bicyclic carbocyclic radical having nine to ten atoms in which at least one ring is aromatic, optionally substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$alkoxy;

and wherein the nitrogens at the 11-position and the 12-position are each substituted with a hydrogen substituent when the bond between the 11-position and the 12-position represented by—is absent;

provided no more than two of A–G comprise nitrogen;

provided $R_1$–$R_3$ and $R_6$–$R_8$ are not each hydrogen;

provided the compound of formula (I) is not 2,3,8,9-tetramethoxy-5,6-diazachrysene or 2,3-3,9-bismethylenedioxy-5,6-diazachrysene; and provided the compound of formula (I) is not a compound of formula (I) wherein D is $NR_e$; when A $CR_3$; B is $CR_s$; E is $CR_cR_d$; F is $CR_f$; and G is $CR_6$;

or a pharmaceutically acceptable salt thereof;

effective to provide an antifungal effect.

* * * * *

UNITED STATES PATENT AND TRADEMARK OFFICE
CERTIFICATE OF CORRECTION

PATENT NO. : 6,740,650 B2
DATED : May 25, 2004
INVENTOR(S) : LaVoie et al.

It is certified that error appears in the above-identified patent and that said Letters Patent is hereby corrected as shown below:

Column 32,
Line 63, after "alkanoyl;" insert -- or --.

Column 33,
Line 51, insert -- ( -- before "$C_1$".

Column 34,
Line 26, delete "($C_6$)" and insert -- ($C_1$- $C_6$) --, therefor.

Column 35,
Line 7, delete "$NR_g$" and insert -- $NR_gR_h$ --, therefor.
Line 13, delete "$R_1$," and insert -- $R_b$ --, therefor.

Column 36,
Line 63, delete "($C_1$- $C_1$)" and insert -- ($C_1$- $C_6$) -- therefor.

Column 37,
Line 12, after "$NR_gR_h$," insert -- $C(=O)R_k$, --.
Line 23, delete "($C_1$- $C_1$)" and insert -- ($C_1$-$C_6$) --, therefor.

Column 39,
Line 13, insert -- bond -- before "represented".
Line 38, delete "trifluoroethyl" and insert -- trifluoromethyl --, therefor.

Column 43,
Line 39, delete "arc" and insert -- are --, therefor.
Line 49, after "2" insert -- , --.

UNITED STATES PATENT AND TRADEMARK OFFICE
CERTIFICATE OF CORRECTION

PATENT NO. : 6,740,650 B2
DATED : May 25, 2004
INVENTOR(S) : LaVoie et al.

It is certified that error appears in the above-identified patent and that said Letters Patent is hereby corrected as shown below:

Column 43,
Line 62, delete "trifluoroethoxy" and insert -- trifluoromethoxy --, therefor.

Column 44,
Line 9, delete "F is $CR_cR_d$" and insert -- E is $CR_cR_d$ --, therefor.
Line 31, delete "F" and insert -- E --, therefor.

Column 46,
Line 19, after "R6" delete ",".
Line 57, delete "$R_8$" and insert -- $R^8$ --, therefor.

Column 47,
Line 60, after "$(C_1-C_6)$" insert -- ) --.

Column 48,
Line 33, delete "$R_3$" and insert -- $R^3$ --, therefor.
Line 46, delete "rind" and insert -- ring --, therefor.

Column 49,
Line 36, after "alkyl," delete "$(C_1-C_6)$" and insert -- $(C_3-C_6)$ --, therefor.
Lines 37 – 40, after "$NR_gR_h$" delete "$COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$,".

Column 50,
Line 56, delete "$NR_c$" and insert -- $NR_e$ --, therefor.
Line 57, delete "$CR_cR_b$" and insert -- $CR_cR_d$ --, therefor.

UNITED STATES PATENT AND TRADEMARK OFFICE
CERTIFICATE OF CORRECTION

PATENT NO. : 6,740,650 B2
DATED : May 25, 2004
INVENTOR(S) : LaVoie et al.

It is certified that error appears in the above-identified patent and that said Letters Patent is hereby corrected as shown below:

Column 51,
Line 5, delete "$R_b$" and insert -- $R_6$ --, therefor.

Column 52,
Line 32, delete "3-3" and insert -- 3-8 --, therefor.

Signed and Sealed this

Twenty-sixth Day of October, 2004

JON W. DUDAS
*Director of the United States Patent and Trademark Office*